United States Patent [19]

Capelli

[11] Patent Number: 5,607,683
[45] Date of Patent: *Mar. 4, 1997

[54] ANTIMICROBIAL COMPOSITIONS USEFUL FOR MEDICAL APPLICATIONS

[76] Inventor: Christopher C. Capelli, 4500 7th St., Kenosha, Wis. 53142

[*] Notice: The term of this patent shall not extend beyond the expiration date of Pat. No. 5,326,567.

[21] Appl. No.: 483,815

[22] Filed: Jun. 7, 1995

Related U.S. Application Data

[63] Continuation of Ser. No. 268,616, Jul. 1, 1994, which is a continuation-in-part of Ser. No. 82,168, Jun. 28, 1993, Pat. No. 5,326,567, which is a continuation of Ser. No. 683,436, Apr. 10, 1991, abandoned.

[51] Int. Cl.$^6$ .......................... A01N 25/00; A01N 59/08; A61L 15/16; A61K 33/14
[52] U.S. Cl. .......................... 424/405; 424/404; 424/422; 424/423; 424/430; 424/431; 424/432; 424/443; 424/445; 424/446; 424/78.06; 424/78.07; 424/609; 424/618; 424/663; 424/669; 424/723; 514/495; 523/122; 604/265
[58] Field of Search .......................... 424/404, 405, 424/422, 423, 430, 432, 443, 486, 618, 609, 669, 663, 722, 723, 678, 679, 680, 670; 514/495; 604/265; 523/105, 113, 122, 111

[56] References Cited

U.S. PATENT DOCUMENTS

| | | | |
|---|---|---|---|
| 3,006,870 | 10/1961 | Steinfatt et al. | 260/2.5 |
| 3,092,552 | 6/1963 | Romans | 424/404 |
| 3,531,433 | 9/1970 | Elmer et al. | 260/45.8 |
| 3,639,575 | 2/1972 | Schmolka et al. | 424/78 |
| 3,645,950 | 2/1972 | Stratta | 260/29.2 |
| 4,054,139 | 10/1977 | Crossley | 128/260 |
| 4,181,786 | 1/1980 | Mune et al. | 525/327 |
| 4,263,424 | 3/1981 | Buckley et al. | 528/85 |
| 4,376,764 | 3/1983 | Schmolka | 424/78 |
| 4,393,871 | 7/1983 | Vorhauer et al. | 609/58 |
| 4,451,447 | 5/1984 | Kaplan et al. | 424/131 |
| 4,451,635 | 5/1984 | Gould et al. | 528/71 |
| 4,460,369 | 7/1984 | Seymour | 601/897 |
| 4,563,184 | 1/1986 | Korol | 514/936 |
| 4,579,731 | 4/1986 | Fox, Jr. et al. | 424/28 |
| 4,581,028 | 4/1986 | Fox, Jr. et al. | 623/2 |
| 4,587,310 | 5/1986 | Ogoe et al. | 525/462 |
| 4,588,400 | 5/1986 | Ring et al. | 514/781 |
| 4,603,152 | 7/1986 | Laurin et al. | 604/265 |
| 4,654,334 | 3/1987 | Williams et al. | 514/184 |
| 4,677,143 | 6/1987 | Laurin et al. | 523/122 |
| 4,693,992 | 9/1987 | Young | 514/11 |
| 4,728,323 | 3/1988 | Matson | 604/304 |
| 4,843,138 | 6/1989 | Tazewell et al. | 528/52 |
| 4,933,178 | 6/1990 | Capelli | 424/78 |
| 4,938,955 | 7/1990 | Niira et al. | 424/618 |
| 5,019,096 | 5/1991 | Fox, Jr. et al. | 623/1 |
| 5,047,448 | 9/1991 | Tanaka et al. | 523/122 |
| 5,073,365 | 12/1991 | Katz et al. | 424/489 |
| 5,292,516 | 3/1994 | Viegas et al. | 424/423 |
| 5,296,518 | 3/1994 | Grasel et al. | 521/176 |
| 5,326,567 | 7/1994 | Capelli | 424/405 |
| 5,328,954 | 7/1994 | Sarangapani | 524/589 |
| 5,344,411 | 9/1994 | Domb et al. | 604/265 |

FOREIGN PATENT DOCUMENTS

| | | |
|---|---|---|
| 3523032 | 1/1987 | Germany. |
| WO-A-92 13906 | 8/1992 | WIPO. |

OTHER PUBLICATIONS

Yanagida et al., "Metal–Ion Complexation of Noncyclic Poly(oxyethlene) Derivatives, I. Solvent Extraction . . . ", Soc. Bulletin Chem., Japan, 50(6):1386–1390, (1977).
Yanagida et al., "Metal–Ion Complexation of Noncyclic Poly(oxyethylene) Derivatives, II. PMR Studies . . . ", Soc. Bulletin Chem., Japan 51(5): 1294–1299, (1978).
Sotobayashi, "Liquid–Liquid Extraction of Some Actinides With Polyehtleneglycol & Derivatives", J. Radioanalytical Chem., 36:145–152, (1977).
Saenger et al., "Wrapping of Metal Cations by Linear Polyethers", Israel J. of Chem., 18–253–258 (1979).
Kolthoff, "Application of Macrocyclic Compounds in Chemical Analysis", Analytical Chem., 51(5):1R–22R.
Frendsdorff, "Salt Complexes of Cyclic Polyethers . . . ", J. Am. Chem. Society, 93(19):(1971).
Pederson, "Cyclic Polyethers and Their Complexes with Metal Salts", J. Am. Chem. Society, 89:26 (1967).
Paik Sung et al., "ESCA Studies of Surface Chemical Compositions of Segmented Polyurethanes", J. Biomed. Mat. Research, 13:161–171, (1979).
Chow et al., "The Extraction and Determination of Thiocyanate Complexes by Use of Polyurethane Foam", Talanta, 30(8) 620–622, (1983).
Weber et al., "Spherical Wrapping of a Linear Polyether around a Cation . . . ", Angew. Chem. Int. Ed. Engl., 18(3): 226–227 (1979).
Weber et al., "S–Shaped Binuclear Cation Complex of a Linear Polyether . . . ", Angew. Chem. Int. Ed. Engl. 18(3): 227–228 (1979).
Hamon et al., "The Caton–Chelation Mechanism of Metal-ion Sorption By Polyurethanes", Talanta, 29:313–326 (1982).
Iwamoto et al., "Structure of Poly(ethylene Oxide) Complexes . . . ", J. Polymer Sci., 6(A2): 1509–1525 (1968).

(List continued on next page.)

*Primary Examiner*—Amy Hulina
*Attorney, Agent, or Firm*—Foley & Lardner

[57] ABSTRACT

Antimicrobial metal-based compositions, which are photostable, non-staining, and which are easily absorbed into lipophilic matrices, contain silver cations, complexed by acyclic polyether polymers through the formation of a "host-guest relationship" where the acyclic polyether is the "host" and the silver cation is the "guest," wherein stabilization of this "host-guest relationship" is accomplished through the use of excess anions. The compositions are useful for topical treatment of infections caused by bacteria, fungus and viruses in humans and animals and for treating medical devices, foams and adhesives to impart infection-resistance.

16 Claims, No Drawings

OTHER PUBLICATIONS

Sotobayashi, "Liquid–Liquid Extraction of Cobalt(II) With Polyethlyeneglycol . . . ", Chem. Ltrs., 77–80, (1976).

Sotobayashi, "Liquid–Liquid Extractions of Varous Metal Ions With Polyethyleneglycol . . . ", Chem. Ltrs., 585–588, (1976).

Thomas et al., "Metal Ion Complexion of Poly(ether)urethanes"; 131–145.

Nathan et al. "Antimicrobial Agents Delivered to Burn Wounds From A Drug–Loaded Synthetic Dressing," *J. Trauma*, 22:12 (1982) 1015–1018.

Asahi Chemical Industry Co. Chemical Abstracts, 113.2 (1990) Abstract No. 12213.

ANTIMICROBIAL COMPOSITIONS USEFUL FOR MEDICAL APPLICATIONS

This application is a continuation of application Ser. No. 08/268,616, filed Jul. 1, 1994, which is a continuation-in-part of Ser. No. 08/082,168 filed Jun. 28, 1993, now U.S. Pat. No. 5,326,567, which is a continuation of Ser. No. 07/683,436, filed Apr. 10, 1991, abandoned.

BACKGROUND OF THE INVENTION

The present invention relates generally to antimicrobial agents and, in particular, to stabilized, metal-based antimicrobial agents suitable for topical applications in the prevention and treatment of infections and as a treatment for medical devices to make them infection resistant.

Antimicrobial agents are chemical compositions that inhibit microbial growth or kill bacteria, fungi and other microorganisms. The antimicrobial activity of inorganic substances is generally related to the ions into which they dissociate. The antimicrobial activity of various metal ions, for example, is often attributed to their affinity for protein material and the insolubility of the metal proteinate formed. Metal-containing salts are thus among the inorganic substances that act as antimicrobial agents.

Infection is a common complication associated with the use of medical devices. Various techniques have been described that incorporate potentially toxic metal ions in the form of metal salts into the materials which make up these medical devices. For example, U.S. Pat. No. 4,603,152, describes an antimicrobial composition useful in providing antimicrobial coatings on medical devices. In this composition, particles of antimicrobial metal compounds are mixed in a polymer matrix and coated onto a medical device to provide antimicrobial protection on that device. U.S. Pat. No. 4,054,139 describes a catheter wherein the exterior and interior surfaces of the catheter have fixed and exposed thereon an effective quantity of silver-bearing, immobile, oligodynamic material which provides the catheter with antimicrobial protection.

The major shortcoming of these methods relates to the poor solubility and consequent slow surface diffusion of the metal salt in the hydrophic and lipophilic material matrix that makes up the medical devices.

Indeed, because the antimicrobial metal salt must be on the surface of the medical device, the antimicrobial protection of the medical implant will last only as long as the metal-salt or compound is on the surface. Additionally, certain metal ions, especially silver ions, are not photostable and, upon exposure to light are reduced to a metal, thereby losing antimicrobial efficacy.

If, on the other hand, metal-salt compounds are added to a separate polymer composition which is then used to coat the surface of the medical device, a problem arises because the coating of an implant with a separate polymer composition may change the dimensions of the medical device. Although this may not be important to medical devices such as wound dressings, a change in size of a medical implant such as a catheter may affect its usefulness.

In U.S. Pat. No. 4,581,028, Fox describes a method for making infection-resistant materials by treating an implant first with an aqueous solution of a sulfonamide salt then with an aqueous solution of a silver salt such as silver nitrate. Fox believed that the silver ion would chelate to the sulfonamide anion on the surface of the polymer and this would provide longer lasting antimicrobial efficacy than would simple treatment of the implant with silver nitrate solution because the silver-sulfonamide salt would solvate into the surrounding environment more slowly.

Romans, U.S. Pat. No. 3,092,552, discloses the use of silver ion as an oligodynamic agent in a therapeutic or surface-treating composition or as an effective means for germicidally protecting an article or surface. Specifically, the disclosed composition is comprised of a low concentration of a silver compound such as silver nitrate or silver oxide, a reducing agent such as starch or sugar, polyethylene glycol (PEG) and urea. This patent further teaches the addition of small amounts of sodium chloride or cupric chloride to the composition to prevent discoloration even when the product is exposed to sterilization procedures and direct sunlight. The presence of metal ions such as copper and/or zinc is thought to stabilize the silver ion, making it more selective in its germicidal activity. Although Romans teaches that the quantities of these metals in the composition should vary, he states that the ratio of copper and/or zinc to silver should be no greater than 2:1.

Another reference teaching pharmaceutical compositions comprised of polyethylene glycol, a metal cation and an anion, is Kaplan, U.S. Pat. No. 4,451,447. Specifically, this reference teaches a composition comprised of cisplatin, PEG and a source of chloride ion, such as sodium chloride, to be used in treating human neoplasms. Kaplan teaches that complexation of the cisplatin with PEG prevents crystallization of the cisplatin during storage and thereby maintains pharmaceutical activity. The compositions do not appear to be photostable in that Kaplan explicitly teaches against exposing the composition to light.

OBJECTS OF THE INVENTION

One object of the present invention is to provide photostable, non-staining antimicrobial metal compositions useful in treating infection and in protecting against infection. Another object is to provide such compositions in hydrophilic or hydrophobic form. Another object of the invention is to provide a method of rendering a polyurethane based foam object antimicrobial.

SUMMARY OF THE INVENTION

These and other objects of the invention are achieved by providing an antimicrobial composition comprising:
 (a) a stabilizing acyclic polyether polymer;
 (b) silver ion; and
 (c) a stabilizing anion, wherein the anion is present in excess with regard to the amount of silver ion, and wherein the antimicrobial composition is photostable.

The invention further provides pharmaceutical preparations comprising the above composition for treating infection in a mammal, or for providing antimicrobial protection to medical devices, wound dressings, sutures and other objects.

The present invention further provides a method of treating infection in a mammal comprising the step of applying to an infected region of the mammal an effective antimicrobial amount of the foregoing composition.

The present invention further relates to a foam composition comprising the foregoing composition and methods of rendering such foam compositions antimicrobial.

DETAILED DESCRIPTION

The present invention relates to antimicrobial metal-based compositions which are photostable, non-staining, and easily absorbed into lipophilic matrices. These antimicrobial metal-based compositions are formed by complexing antimicrobial metal cations with acyclic polyether polymers through the formation of a "host-guest relationship" wherein the acyclic polyether is the "host" and the metal cation is the "guest" and the stabilization of this "host-guest relationship" is accomplished through the use of excess halide ions, preferably anions, and a minimal amount of solvent.

The preferred metal-based compositions of the present invention have at least the following components:

(a) a stabilizing acyclic polyether polymer;

(b) silver ion; and (c) an excess of anions relative to the concentration of the silver ion.

A minimum amount of solvent may be used to conveniently promote solvation of the silver salts and the halide salts.

In providing a metal-based antimicrobial composition that can be used both topically and in treating medical devices, the present invention makes metal cations neutral and more lipophilic, thereby enabling the metal salts to solvate and diffuse out of the lipophilic matrix. This is accomplished by complexing antimicrobial metal cations with acyclic polyethers in a "host-guest relationship" similar to the basic technology found in crown ethers.

Crown ethers are cyclic ethers containing several (four, five, six, or more) oxygen atoms. They are neutral molecules that can transfer ionic compounds into an organic phase either from a water phase or, more commonly, from solid crystal. The molecular structure of a crown ether looks like a doughnut: facing into the hole are the oxygen atoms; facing outward are the $CH_2$ groups. This structure produces a molecule which has a hydrophilic interior and a lipophilic exterior.

Unfortunately, crown ethers are impractical for antimicrobial purposes for several reasons. First, they may cause fatal metabolic disturbances in the subject being treated because, once dissociated from a metal cation, they may chelate a variety of other metabolic cations, especially trace metal ions which are essential to metabolism in the human body. Another drawback is that the metal cation may be dissociated too slowly to form an effective concentration level.

Thus, the present invention is based on the discovery of a method for making metal cations more lipophilic, so that they may more easily diffuse in and out of lipophilic matrices using a "host-guest relationship", without the inherent problems associated with the use of crown ethers. That is, the problems associated with the use of crown ethers have been solved by using acyclic polyethers, e.g., polyethylene glycol(PEG) which has the general formula $HO(CH_2 CH_2 O)_n H$, wherein n is an integer equal to 2 or greater. Polyethers, especially PEG, are similar in many of their properties to crown ethers except that they are linear rather than cyclic.

Polyethers are known to solvate and chelate cations, including metal cations. Under special circumstances, it has been found that acyclic polyether polymers can act like crown ethers in forming a "host-guest relationship" with cations. It has been described in the literature, through experiments using single crystal x-ray analysis, that low molecular weight acyclic polyethers can form metal ion complexes with metal salts in either a relatively random or "S" configuration or in a relatively ordered or coiled configuration. Weber, G. et al., *Angew. Chem, Int. Ed.*, 12:227 (1979); Weber, G. et al., *Angew. Chem., Int. Ed. Eng.*, 18:226 (1979).

The special circumstances which are required for an acyclic polyether polymer to form a "host-guest relationship" with a metal cation are not well understood. It is believed that the conditions necessary for the formation of acyclic polyether metal complexes and the factors influencing their stability are similar to those factors necessary for the formation and stability of cations chelated by crown ethers. These factors include (a) the relative size of the cation, (b) the number of oxygen atoms in the polyether ring, (c) the coplanarity of the oxygen atoms, (d) the symmetrical placement of the oxygen atoms and, (e) the electrical charge on the ion. Because acyclic polyether polymers are in a random shape, the formation of a "hole" in which the cation is a "guest" has to be induced in the acyclic polyether polymers. Crown ethers, on the other hand, already have a "hole" in their structure.

Forming a stable composition consisting of metal cations and polyether polymers is not as simple as merely putting a metal cation salt into solution in a polyether polymer. For example, if one mixes a small quantity of silver nitrate solution with liquid polyethylene glycol (PEG) (400 dalton molecular weight) the resultant solution will not be stable. In such a case, lack of stability for the silver nitrate/PEG solution is indicated by the solution turning a dark brown/black color which is evidence of photo-instability. This dark color is the result of the silver ion in the solution being reduced to metallic silver, induced by light, and indicates that the silver ion is not stabilized.

Likewise, if one puts a small quantity of silver nitrate solution into liquid polyethylene glycol (400 molecular weight), followed by an equimolar amount of a sodium chloride solution, not only will silver chloride precipitate out of the polyethylene glycol solution, but it also will change to a darker color on exposure to light.

Surprisingly and unexpectedly, conditions have now been discovered that will produce stable silver ion solutions. If one puts a 10-fold molar excess of sodium chloride solution into a silver nitrate/PEG solution, then no precipitation of silver chloride occurs and the solution remains clear, color-stable, and non-staining. These are all indications that a "host-guest relationship" has developed between the silver cation and the PEG.

This principle is also demonstrated when one puts a small quantity of silver nitrate solution into liquid polyethylene glycol (400 molecular weight), followed by an equimolar amount of a sodium bromide solution to form a silver bromide solution. Again, not only will a precipitate form (presumably silver bromide) in the liquid polyethylene glycol solution, but it also will change to a darker color. However, if instead of putting an equimolar amount of a sodium bromide solution into the silver nitrate/PEG solution, one puts in a 6-fold molar excess of sodium bromide solution into the silver nitrate/PEG solution, no precipitation occurs and the solution remains clear, color stable, and non-staining. Again, it is believed these are all indications that a "host-guest relationship" has developed between the silver cation and the PEG and these results are unpredictable from the theories and results presented in the prior art.

As used herein, the terms "color stable" and photostable" mean that the claimed compositions do not darken upon exposure to sunlight or a plant light for at least 24 hours, preferably 72 hours and more preferably, one week, one month, six months, or indefinitely. Thus, the compositions have long-term photostability.

ACYCLIC POLYETHERS

Suitable acyclic polyethers for use in compositions according to the invention include polyethylene glycol, H(OCH$_2$CH$_2$)$_n$OH, polypropylene glycol, HO(C$_3$H$_6$O)$_n$H, and polytetramethylene glycol, HO(CH$_2$CH$_2$CH$_2$CH$_2$O)$_n$H. The preferred polyether polymer is polyethylene glycol.

Polyethers in the form of copolymers may also be used, such as those marketed under the Trademark "Pluronics" by BASF. These copolymers typically have the combination of polyethylene glycol and polypropylene glycol polymer blocks in a number of configurations such as PEG-PPG-PEG, PPG-PEG-PPG, etc., with an average molecular weight of 1,000 to 30,000 daltons. In these copolymers, the PEG polymer block can make up 10–90% of the total copolymer. Likewise, the PPG polymer block can make up 10–90% of the total copolymer. The copolymer may also be a polyethylene glycol block copolymer. An example of such a copolymer is a poloxamer, as described in Example 23, below. The polyether of the present invention may also be a polyethylene glycol conjugate, such as nonoxynol (polyethyleneglycol mono (nonylphenyl) ether), as described in Example 21, below.

The molecular weight of the polyether molecule can vary depending on the desired form of the end product. For a low viscosity composition in the form of a fluid, a low molecular weight (approximately 200–10,000 daltons) polyether composition can be used. For a high viscosity fluid composition or a solid composition, a medium molecular weight (approximately 1,000–50,000 daltons) polyether composition can be used. Of course, viscosities of the final composition can be increased by the addition of viscosity enhancers well known in the art. For a film or an adhesive composition, a high molecular weight (approximately 50,000–1,000,000 daltons) polyether composition can be used.

The preferred polyethers are those of the glycol polyether class. These polyethers have the greatest ability to form a "host" configuration. That is, they are not structurally constrained by their carbon backbone so they may more easily form a stable coil configuration about silver cation. Polypropylene glycol may form a "host" configuration. However, since it has an extra methyl group projecting from its carbon chain, it is believed to be more hindered than PEG and therefore less suitable.

As noted above, the silver ion is thought to be stabilized through the formation of a "host guest" relationship with the polyether. One possibility is that the polyether becomes the "host" through the formation of a pseudo-crown ether. That is, the polyether forms a coil the center of which has ether groups internalized and carbon groups externalized. The size of the hole formed within a coil will influence the ability of the polyether to form a "host-guest" relationship with the silver ion. If the hole is too large, the silver ion will not be very stable; if the hole is too small, the silver ion will not be able to form the new "cation".

Alternatively, the polyether could form coiled tubes, similar to starch and sequester linear silver halide salts therein.

The molecular length of the polyether will play an important role in stabilizing the cation. If the polyether is small, it will not be able to form a complete coil or will form a coil which is too small for the formation of a "host-guest" relationship with the silver cation. Based on the size of the silver cation (2.52 angstroms), it is estimated that a polyether with at least 6 ether groups is required. Six ether groups would give a polyether polymer a molecular weight of 288 daltons. Polyether glycols are available usually as a mixture of several molecular weights in a Gaussian distribution centered at a specific molecular weight. For example, PEG 300 has an average molecular weight of 300 daltons with a Gaussian distribution centered at 300 daltons of PEG's with molecular weights both below and above 300 daltons.

Thus, in order to stabilize the silver cation, the preferred PEG's should have a molecular weight of 300 daltons or greater. Because PEG 300 will have a portion of its composition made up of smaller PEGs, it would not be expected to stabilize as much silver cations because only those PEGs with a molecular weight greater than 288 will contribute to the formation of the "host-guest" relationship. Likewise, PEG 200 will have the majority of its polymers with a molecular weight being less than 288, and therefore would not be expected to be able to stabilize more than a small amount of the silver cation.

Thus, the preferred polyether is polyethylene glycol having a molecular weight in the range of 200 to 100,000 daltons, most preferably in the range of from 300 to 10,000 daltons.

ANTIMICROBIAL METAL CATIONS

The particularly preferred metal cation of this invention is silver ion. However, the teachings of this invention are applicable to the use of other metal cations. These metal cations include all metal compounds that are physiological, antimicrobial compounds, in particular, metal compounds which are "oligodynamic". The term "oligodynamic" is used to denote a metal agent, particularly a metal salt or a metal ion it yields upon dissociation, that has antimicrobial activity in very small quantities. The "oligodynamic" metals include the precious metals, such as silver, gold and platinum, and other metals such as copper, zinc, cerium, and gallium. The preferred oligodynamic metal ion is silver ion. A review of oligodynamic metals can be found in *DISINFECTION. STERILIZATION AND PRESERVATION.* Chapters 24 and 28 (Lea & Fibiger, Philadelphia, 1968), the contents of which are hereby incorporated by reference.

The amount of stabilized metal cation used in the composition is determined by the amount of polyether present, the size of the polyether, and the amount of anions present. The basis for complexing of the metal cation is the formation of a "host-guest relationship" between the polyether polymer and the metal cation. The optimal stability is obtained when there are at least 5–8 ether groups per metal cation. Thus, from a theoretical standpoint, a nonhindered polyether molecule with 6 ether groups should bind 1 metal cation ion at its upper limit, i.e., 1 mole of polyether molecules that have 6 ether groups per molecule should be able to stabilize 1 mole of metal cations. Any amount of metal cation below this amount is acceptable. Metal cations in excess of this amount will precipitate with the anions in the composition and will not be stable.

When the polyether composition is composed of molecules which have substantially larger molecular weights (either alone or as part of a larger molecule such as a polyether urethane), and therefore have greater than 6 ether groups per molecule, the amount of cation that can be stabilized is more closely related to the number of polyether molecules than to the number of ether groups per molecule. For example, a polyether that has 20 ether groups per molecule will more likely bind a single metal cation than 3 metal cations as previously discussed. This is probably a result of the conformational limitations of the polyether molecule about the metal cation.

The preferred concentration of metal cations in a polyether composition is in the range of $1 \times 10^{-6}$ to 1 meq/gram of metal cation to polyether polymer and most preferably, $1 \times 10^{-3}$ to $1 \times 10^{-1}$ meq/gram of metal cation to polyether polymer.

In the preferred embodiment, as noted above, silver ions are used. The silver ions may be derived from an aqueous-based silver nitrate solution. Alternatively, the source of silver ions may be essentially non-water soluble silver salts, i.e., the solubility of the silver salt being less than 1 gm/100 gm water. See Examples 31–39, below.

ANIONS

To form a "host-guest relationship" between the antimicrobial metal cation and the polyether molecule, an excess of anions is preferred. Suitable anions for promoting a "host-guest relationship" include chloride, bromide, iodide and thiocyanate, the most preferred anion for physiological applications being chloride. Chloride is preferred because the chloride ion is the most abundant anion in the human body and has the lowest toxicity.

Any source of the anion may be used to provide an excess amount of the anion. Suitable sources of anions include the inorganic salts which are physiologically tolerable. These include, but are not limited to, sodium chloride, potassium chloride, sodium bromide, potassium bromide, calcium chloride, potassium iodide and sodium thiocyanate. The preferred sources of anions are sodium chloride, hydrochloric acid or a mixture thereof.

The amount of anions to be added to the composition will depend on the amount of metal cations in the final polyether composition and which anion is being used. Due to charge density, hydrophobicity and other factors, certain anions are better at stabilizing the silver/polyether complex than other anions. For example, iodide is better than bromide which is better than chloride for stabilizing the silver polyether complex, so that the amount of excess iodide required is less than the amount of excess chloride anions. Thus the ratio of equivalents of anions to equivalents of metal cations is greater than 1 to 1.

The preferred ratio of equivalents of anions to equivalents of metal cations is between 2 to 1 and 40 to 1. The anion to cation ratio may be as high as 100:1. Ratios of equivalents of anions to equivalents of silver cations for various anions are as follows:

— Chloride Anions to Silver Cations: greater than 4 to 1, preferably 8 to 1 and most preferably 9 to 1.

— Bromide Anions to Silver Cations: greater than 2.1 to 1, preferably 3 to 1 and most preferably 3.5 to 1.

— Iodide Anions to Silver Cations: greater than 1.1 to 1, preferably greater than 1.2 to 1 and most preferably greater than 1.4 to 1.

— Thiocyanate Anions to Silver Cations: greater than 3.5 to 1, preferably greater than 4 to 1 and most preferably greater than 4.5 to 1.

It should be noted that the ultimate amount of anions used in the composition is dependent on the concentration of anions and what polyether is used. Polyethylene glycols have a tendency to "cloud" when a high concentration of salt is used. That is, the PEG will precipitate out of solution. If the PEG precipitates out of solution, it will be more difficult to form a stabilized silver compound.

SOLVENT

A certain amount of solvent may be present in the composition according to the invention. It is used as a convenience to promote the solvation of the salts that provide the antimicrobial metal cations and the salts used to supply the excess amount of anions, and these salts are usually added as solutions in the solvent. Any solvent may be used which is physiologically compatible and also compatible with the metal cations, polyether polymers and the salts that provide the anions. The preferred solvents are, alcohol, acetone, water and a mixture thereof. The most preferred solvent is water.

To promote the formation of the "host-guest" relationship between the polyether molecule and the silver cation, the amount of solvent used is dependent on the anion used and the amount of anion. If the concentration of the anion within the water falls below a certain concentration, the formation of the stabilized silver composition is less likely to occur. If the anion (such as iodide) strongly promotes the formation of a silver complex, then the concentration of iodide in the water can be low. If the anion, (such as chloride) weakly promotes the formation of a silver complex, then the concentration of chloride in the water should be high.

The amount of water to be added can be high so long as the concentrations of salts are maintained. The preferred concentration of water in the final composition is between 1% and 60% and most preferably between 2% and 20%. The preferred concentration of anions within the solvents for the various anions are as follows:

— Chloride/Water Concentration: greater than 1.2 meq/ml and preferably greater than 1.6 meq/ml and most preferably greater than 2.0 meq/ml.

— Bromide/Water Concentration: greater than 0.2 meq/ml and preferably greater than 0.4 meq/ml; and most preferably greater than 0.6 meq/ml.

— Iodide/Water Concentration: greater than 0.002 meq/ml and preferably greater than 0.0025 meq/ml and most preferably greater than 0.004 meq/ml.

— Thiocyanate/Water Concentration: greater than 1.5 meq/ml and preferably greater than 1.8 meq/ml and most preferably greater than 2.0 meq/ml.

METHOD OF MAKING THE COMPOSITION

Because a number of variables are involved in making a stabilized silver composition of this invention, it is probably easiest to empirically determine the final composition using the guidelines of this disclosure. One approach for making a stabilized silver composition is as follows:

1. Preparing the polyether: the first step is the synthesis of the particular polyether composition. An example would be the synthesis of a low molecular weight polyether urethane. The synthesis of polyether urethane is well known to the art. This synthesis step may be avoided if the polyether molecule is readily available and is in need of no further modification. For example, one could use an ethylene glycol polymer with a molecular weight of 400 which is available from a number of sources.

2. Making the anion solution: an anion from the group consisting of chloride, bromide or iodide should be chosen. If the stabilized silver composition is to be used on humans, the preferred anion is chloride. After choosing the anion, a water solution of the anion salt should be made. The concentration of the final anion solution should be above the minimum concentration as discussed above to promote the formation of the "host-guest" relationship.

3. Making the silver cation solution: Make up 1–2 meq/ml silver nitrate solution in water. Alternatively, the proper amount of the silver salt is weighed out on a balance and added directly to the polymer.

4. Determining the amount and concentration of anions that can be used: polyethers in the presence of appreciable amounts of dissolved salts will often show "cloud points" or temperatures above which they tend to precipitate out of solution. Since it is more difficult to form a stabilized silver composition above the "cloud point", it is important to determine the maximum concentration of dissolved anions that can be used in the final composition. For the final composition, a concentration of dissolved anions below this level should be used.

5. Making the final composition:

a. Stir the polyether in a beaker, heating if necessary. If the polymer is a solid at room temperature, it is heated until it melts.

b. Add the anion salt solution. Use the amount determined in Step 4. Mix completely.

c. Add the silver nitrate solution in small increments. Upon adding the silver nitrate solution, a precipitate will form. This precipitate will slowly dissolve with stirring. After the precipitate has dissolved, add another increment of silver nitrate solution. If the precipitate does not dissolve within 2 hours, then the maximum silver that can be used in the composition has been found. Since this maximum is dependent on the anion, the ratio of anion to cation and the polyether being used, it is best determined by this empirical method.

d. Repeat steps (a) and (b) but add the amount of silver nitrate solution below the maximum determined in step (d). Mix. If heated, the polyether solution should be cooled to room temperature.

The silver compositions made from the above procedure are photostable and stain resistant. They may be stored in a clear container in sunlight without discoloration, and are stable to ultraviolet light and even to a sterilizing beam of gamma radiation.

The lipophilic nature of the silver compositions of the present invention render them miscible in a wide range of organic solvents such as polymers or oils and organic compositions. This provides for the production of compositions containing a mobile form of an inorganic salt. This is advantageous for applications in addition to the antimicrobial applications disclosed herein.

APPLICATIONS OF THE METAL-BASED COMPOSITIONS

Topical Applications

When in the form of a solution, cream or ointment, the metal-based antimicrobial compositions of this invention can be used topically on skin, in wounds, in the eyes, nose or the mouth for the treatment or prevention of a large number of topical infections. For the treatment or prevention of infections in wounds, the composition can be applied to the wound site by standard methods known to the industry. One method is to apply the composition by gloved hand. Wound dressings may be used in conjunction with the composition as currently practiced in the treatment of topical infections. The composition offers long term antimicrobial protection and helps prevent the desiccation of the wound site. In the treatment of eye infections, the composition, in the form of a solution or a cream, can be applied to the lower eyelid of the patient using standard techniques or the composition may be in the form of an eyewash and applied using standard techniques. In the treatment of mouth infections, including gingivitis, the composition in the form of a solution or cream can be applied using a sponge applicator or a toothbrush. The compositions of the invention may also be in the form of a solution and used for infusing into a body cavity and thereby treating infection.

The compositions of this invention offer several major advantages for the topical application of metal ions to the patient. First, the compositions do not contain any antibiotics to which the patient may be sensitive. Second, the risk of having bacteria develop resistance to an antibiotic—the creation of a highly resistant strain of microbe—is substantially eliminated. Also, especially in the case of antimicrobial silver ions, the composition will not stain the patient's skin or clothes, a problem which is associated with the use of prior art metal-based compositions or metal salts. Fourth, because the stabilization of the metal ion is thought to be through the formation of a "host-guest relationship" between the metal cation and the polyether polymer, and this complexation is more lipophilic than other metal salts, there is a higher likelihood that the metal cation will be able to penetrate the skin more efficiently. This is because the skin, in its simplest description, is a lipophilic matrix. Being able to deliver metal cations more easily into skin will make the metal cations more effective as topical antimicrobial agents. An example is the use of a zinc/polyether composition for the treatment of fungal diseases. Since fungi reside within the upper layers of the skin, a zinc composition that can more easily penetrate this layer would be more effective.

The compositions of the invention may be in a hydrophilic liquid, e.g., a cream, ointment or solid, such as that described in Examples 24, 26, 27 and 28, below. Hydrophilic compositions have the advantage of being easy to remove with routine washing.

Alternatively, the compositions of the invention may be in a hydrophobic form so as to be suitable for use in areas exposed to excess moisture or water. Such compositions comprise the above-described antimicrobial composition in hydrophobic substance such as USP white petrolatum wax, oil, etc. Varying the proportions of the antimicrobial composition to the hydrophobic substance will vary the degree of hydrophobicity of the final composition.

The efficacy of hydrophobic antimicrobial compositions produced in accordance with the present invention are unexpected because one would not expect silver ions to be able to diffuse out of such a composition. However, in Example 29, below, applicants describe the production of a hydrophobic silver-based ointment which is surprisingly light-stable and yet is antimicrobial.

PRODUCING INFECTION-RESISTANT MEDICAL DEVICES

Due to their light-stability, low toxicity and increased lipophilicity, the metal cation/polyether compositions of this invention are usefully applied to medical devices to make them resistant to microbes in mammals, especially humans. As discussed above, medical devices are a major source of infection because microbes colonize their surfaces. The patient's body has a difficult time eradicating bacterial colonization on the surface of medical devices where there is poor vascularization and the possible formation of a protective biofilm. As a result, medical devices can act as reservoirs for microbes seeding into the patient's body, and thereby leading to infection. If the material of a medical device can be made infection-resistant, the safety of the medical device to the patient will be enhanced substantially.

The metal compositions of this invention, preferably in the form of a low viscosity liquid, can be used to treat medical implants, wound care devices, and body cavity and personal protection devices. The medical implants that can be treated include, but are not limited to, urinary catheters, intravascular catheters, dialysis shunts, wound drain tubes, skin sutures, vascular grafts and implantable meshes, intraocular devices, heart valves, and the like. Wound care devices include, but are not limited to, general wound dressings, non-adherent dressings, burn dressings, biologic graft materials, tape closures and dressings, and surgical incise drapes. Body cavity and personal protection devices include, but are not limited to, tampons, sponges, surgical and examination gloves, and toothbrushes. Birth control devices include, but are not limited to, IUD's and IUD strings, diaphragms and condoms.

The metal compositions of this invention in the form of a high viscosity liquid, can be used to render adhesive materials antimicrobial. Examples of such adhesives include polyurethane adhesives which are used as backings for wound dressings. The preferred adhesive of the present invention is that which is described in U.S. patent application Ser. No. 07/365,313 now U.S. Pat. No. 5,045,601, which is hereby incorporated by reference. This adhesive composition is comprised of a polymer adhesive which is soluble or dispersible in water and is low-temperature curable to form a solid which is single-phase at ambient temperature, pressure-sensitive, dermatologically acceptable, moisture vapor-permeable and resistant to dissolution when exposed to water.

The method of treating medical devices to make them infection resistant will depend on the material that makes up the medical devices. For devices that are made up of cellulose type polymers, such as cotton gauze pads for wound care devices and surgical gowns or sponge materials, the metal cation/polyether composition can be applied through spraying, dipping or any other standard method known to the art. The metal/polyether composition is easily absorbed by the cellulosic material or sponge materials and makes the device infection-resistant. An important advantage of using the composition of this invention in devices which are absorptive, is that it will not discolor upon exposure to light.

For medical devices such as catheters, vascular grafts, surgical gloves, etc., which are comprised of lipophilic polymers, treatment can be accomplished in a similar fashion as described above. However, one of the major advantages of the composition of this invention is the ease with which the composition can be absorbed into lipophilic polymer matrices. These polymer matrices may act as reservoirs for the metal cation/polyether compositions and thereby provide long-term protection to the medical device.

The lipophilic polymers that are easiest to treat are those which have amorphous regions within their molecular makeup -and are not strictly crystalline. That is, lipophilic polymers that can readily accept a plasticizer are more likely to absorb the metal cation/polyether compositions of this invention. Examples of preferred lipophilic polymers include silicone, polyurethane, polyethylene, nylon, polyvinyl chloride, polyvinyl alcohol, the cellulosic polymers, polyvinyl acetate, polyesters, and acrylics.

A suitable procedure for treating devices comprised of lipophilic polymers involves applying the metal cation/ polyether composition to all surfaces and letting the composition absorb into the material. This may be accomplished by painting, spraying or dipping the medical device into the composition. In some cases, this may involve infusing the composition into a device. The preferred method is to dip or bathe the device to be treated in a bath containing the metal/polyether composition. The length of time the device is kept in the composition is dependent on many factors including the material being treated, the dimensions of the material and the temperature of the solution, and can range from a few seconds to 24 hours. After the device has been treated and given time to absorb the composition into the matrix, the excess composition is eliminated from the surface of the device. This can be accomplished by washing the treated device in a water bath for a few seconds, wiping the excess composition off the surface with an absorptive material, such as paper towels or by blowing the excess off the surface with a stream of air.

After the device has been treated, it will be infection-resistant against a broad spectrum of microbes. Since the device is light stable, no special packaging requirements will be necessary.

The compositions of the present invention may be used in the preparation of antimicrobial foam objects. Foam objects are extensively used in wound care because of their ability to provide a moist wound microenvironment which promotes the body's healing process at the wound site. Thus, it is advantageous to produce foam objects that contain stabilized silver ions in a moist environment that is subject to contamination by microorganisms in the foam matrix.

The most widely used foam objects utilized in wound care consist of polyurethane foam matrices. The polyurethane foam objects are typically made by reacting a polyurethane prepolymer with a compound that is reactive to the polyurethane prepolymer, resulting in chain extension and crosslinking to form the polymer. The foam matrix is created by standard means, including injecting a gas into the mixture during the polymerization step or by using water as the reactive compound to cause the polymerization of the polyurethane prepolymer. Water reacts with isocyanate groups in the polyurethane prepolymer resulting in the formation of carbon dioxide which creates the foam matrix.

In accordance with the present invention, one method for making a silver foam object using the antimicrobial compositions of the present invention is to infiltrate a stabilized silver composition of the present invention directly into the foam matrix by:

• applying the stabilized silver composition by spraying, painting, coating, etc., to the surface of the foam matrix;

• submerging the foam matrix into a volume of stabilized silver composition;

• wicking the stabilized silver compositions into the foam matrix;

as well as other standard means of applying solutions to foam matrices.

While this method can produce foam objects that contain silver, it is less than optimal because it requires a "secondary" step during the production of the silver foam. That is to say, an additional manufacturing step needs to be performed after the foam has been produced to incorporate the silver composition. This "secondary" step results in the need for additional equipment, i.e., sprayers, coaters, etc. to apply the antimicrobial compositions as well as increase the costs.

Another method for imparting antimicrobial protection to polyurethane foam objects by incorporating antimicrobial compositions of the invention during the polymerization of the foam matrix, comprises the steps of:

(a) making an antimicrobial composition in accordance with the present invention;

(b) directly incorporating said antimicrobial composition during the production of the foam matrix; and (c) drying the foam matrix.

Alternatively, foam objects may be rendered antimicrobial by (a) incorporating silver ions and stabilizing anions during the production of the foam matrix and (b) drying the foam matrix.

These methods to produce polyurethane foam objects are new and totally unexpected because it is not expected that the antimicrobial compositions consisting of the compositions of the invention would maintain their ability to stabilize the silver ions and remain photostable after being present during the polymerization of the polyurethane prepolymer. In fact, given that the majority of said acyclic polyethers of the invention are reactive to the polyurethane prepolymer and can be incorporated directly into the foam matrix, it could be expected that the silver would lose its stability resulting in silver foams that were not photostable. Thus, the method of incorporating the antimicrobial composition of the invention is not only unexpected, but counterintuitive.

One important advantage of the above-described new method of imparting antimicrobial protection to polyurethane foam objects is that it will eliminate the need to have a "secondary" manufacturing step when producing silver-based foam objects saving time, money and the need for additional equipment.

Of course, the invention is not limited to polyurethane foams, as the skilled artisan would be aware of other non-polyurethane foams encompassed by the invention. Indeed, the examples illustrate applications using other polymers and provide guidance to the skilled arisan.

The examples which follow further serve to illustrate the present invention and should not be considered as limiting its scope.

EXAMPLE 1 Stable Liquid Silver-Based Antimicrobial Composition

To demonstrate the antimicrobial efficacy and the light stability of a silver based antimicrobial composition of this invention, 18.2 grams of polyethylene glycol (molecular weight: 400) was mixed with 0.18 ml of a 1 meq/ml solution of silver nitrate dissolved in water and 1.62 ml of a 2 meq/ml solution of sodium chloride in water. The ratio of chloride anions to silver cations was 18 to 1. This composition is hereinafter referred to as "Silver Composition 1". The total amount of water in the final composition was 9.8%. The final composition was clear, with no precipitate, and was very light-stable. Putting some of this composition on a cotton gauze pad and exposing this pad to light caused no discoloration of the gauze pad. This composition has a low viscosity and can be used topically on the skin for the prevention and treatment of infections or can be used to make medical devices infection resistant by painting, spraying or dipping.

EXAMPLE 2 Effect of PEG Molecular Weight on Stability of Silver

Silver ion compositions were made which differed only in the molecular weight of the PEG used. Each study was performed by taking 25 grams of a PEG or ethylene glycol, first adding 0.250 ml of an aqueous 1 meq/ml silver nitrate solution, and then adding 2 ml of a 3 meq/ml sodium chloride solution. The solutions were observed to see if they formed a clear solution without any precipitate and stayed photostable. Ethylene glycol, and PEG's with average molecular weights of 200, 300, 400 and 600 were used.

Silver compositions which used PEG's with average molecular weights of 300, 400 and 600 formed photostable solutions which contained no precipitate. Silver compositions which used either ethylene glycol or a PEG with an average molecular weight of 200, formed mixtures containing a large amount of precipitate, which were photo-unstable upon exposure to sunlight. The PEG 200 solution had less precipitate than the ethylene oxide composition. This may be the result of the higher molecular weight PEG's within the PEG 200 which formed complexes.

EXAMPLE 3 Unstable Liquid Silver-Based Antimicrobial Composition

To demonstrate that the excess of anions relative to metal cations are of prime importance in providing stability of the antimicrobial compositions, two other compositions were made that were equivalent to Silver Composition 1, except for the amount of anions present. In the first composition, no stabilizing anions was used. In the second composition, an equivalent amount of anions was used.

The first composition (2a) was made by taking 18.2 grams of polyethylene glycol (molecular weight: 400) and mixing, under the same conditions as in Example 1, with 0.18 ml of a 1 meq/ml of an aqueous silver nitrate solution. To this was added 1.62 ml of water which contained no sodium chloride. The ratio of chloride anions to silver cations was 0 to 1. The total amount of water in the composition was 9.8%.

The second composition (2b) was made by taking 18.2 grams of polyethylene glycol (molecular weight: 400) and mixing, under the same conditions as in Example 1, with 0.18 ml of an aqueous 1 meq/ml silver nitrate solution. To this was added 1.44 ml of water which contained no sodium chloride and 0.18 ml of an aqueous 1 meq/ml sodium chloride solution. The ratio of chloride anions to silver cations was 1 to 1. The total amount of water in this composition was also 9.8%.

Composition (2a) formed a clear solution with no precipitate. However, on exposure to light, the composition turned a light brown color. Over time, the composition continued to darken in color. Applying some of this composition on a cotton gauze pad and exposing this pad to light caused the gauze pad to discolor. The discoloration of the gauze pad was not removed with a washing with water, indicating that the discoloration was permanent.

Composition (2b) formed a clear solution that developed a precipitate immediately after the addition of the sodium chloride solution. The precipitate settled to the bottom of the container over 24 hours. Upon exposure to light, the precipitate in the composition turned a light brown color. Over time, the precipitate in the composition continued to darken in color.

EXAMPLE 4 Stable Liquid Silver-Based Antimicrobial Composition

To demonstrate that the principle of the invention is not dependent on which anion is used, silver compositions were made in which bromide was chosen as the stabilizing anion. In this example, 18.2 grams of polyethylene glycol (molecular weight: 400) was mixed with 0.18 ml of an aqueous 1 meq/ml solution of silver nitrate, dissolved in water, and 1.62 ml of an aqueous 1 meq/ml sodium bromide solution was added. The ratio of bromide anions to silver cations was 9 to 1. The total amount of water in the final composition was 9.8%. The resulting composition was clear with no precipitate, and was light-stable. When this composition was applied to a cotton gauze pad and exposed to light, no discoloration occurred.

EXAMPLE 5 Unstable Liquid Silver-Based Antimicrobial Composition

Again, to demonstrate that excess of anions is of prime importance in stabilizing the antimicrobial compositions of this invention, two other compositions were made that were equivalent to those described in Example 4 except for the amount of bromide anions present. In the first composition, no bromide anions was used. In the second composition, an equivalent amount of bromide anions to silver cations was used.

The first composition (4a) was made by taking 18.2 grams of polyethylene glycol (molecular weight: 400) and mixing, under the same conditions as in Example 4, 0.18 ml of an aqueous 1 meq/ml silver nitrate solution. To this was added 1.62 ml of water which contained no sodium bromide. The ratio of bromide anions to silver cations was 0 to 1. The total amount of water in the composition was 9.8%.

The second composition (4b) was made by taking 18.2 grams of polyethylene glycol (molecular weight: 400) and mixing, under the same conditions as in Example 4, with 0.18 ml of an aqueous 1 meq/ml silver nitrate solution. To this was added 1.44 ml of water which contained no sodium bromide and 0.18 ml of an aqueous 1 meq/ml sodium bromide solution. The ratio of bromide anions to silver cations was 1 to 1. The total amount of water in the composition was 9.8%.

Composition (4a) gave the same results as composition (2a). Composition (4b) provided results similar to those with (2b). The resultant composition was a clear solution that developed a precipitate immediately after the addition of the sodium bromide solution. The precipitate settled to the bottom of the container within 24 hours. Upon exposure to light, the precipitate in the composition turned a darker color and continued to darken over time.

Compositions (4a) and (4b) were repeated except that potassium iodide was used in place of sodium bromide. The results were similar to those in Example 4. When the ratio of equivalents of anions to equivalents of metal cation was 1 to 1 or less, no stability was noted for either the chloride, bromide, or iodide anions. At appropriate ratios greater than 1 to 1, the silver cation/polyether compositions of the invention were all clear, light-stable and non-staining.

Table 1 summarizes the results of the light stability of the compositions made in the above examples. These photostability experiments were performed by taking bottles containing the compositions and exposing them to a plant growth light (Lifelite, Model No. 8040, 118 V, 60 Hz, 70 W) to simulate direct sunlight exposure. The samples were exposed continuously under the same conditions. The results of this experiment demonstrate that the compositions from Examples 1 and 4 were photostable and that the compositions from Examples 3 and 5 were not.

It should be noted that, even after 6 months of exposure to sunlight, no change occurred in the appearance of the compositions of Examples 1 and 4. This indicates that the compositions were light stable over long periods of time.

TABLE 1

| Effect of Cation to Anion Ratio on Light Sensitivity | | | | |
| --- | --- | --- | --- | --- |
| | Cation:Anion | Period of Exposure | | |
| Composition | Ratio | 1 HR | 24 HR | 72 HR |
| Example 2a | 1:0 | light brown | dark brown | dark |
| Example 2b (Cl) | 1:1 | light brown | dark brown | dark |
| Example 1 | 1:18 | clear | clear | clear |

TABLE 1-continued

| Effect of Cation to Anion Ratio on Light Sensitivity | | | | |
| --- | --- | --- | --- | --- |
| | Cation:Anion | Period of Exposure | | |
| Composition | Ratio | 1 HR | 24 HR | 72 HR |
| (Cl) Example 4b (Br) | 1:1 | light brown | dark brown | dark |
| Example 3 (Br) | 1:9 | clear | clear | clear |

Table 2 summarizes the results of studies examining the staining capability of the compositions in Examples 1 through 5. As mentioned above, the staining experiments were performed by taking a sample of the silver antimicrobial compositions from the previous examples and applying them to soak in a white cotton gauze. These gauze samples were placed at a distance 6 inches from the plant growth light which simulated direct sunlight exposure, to determine if discoloration and staining occurred. The results of these experiments are summarized in Table 2 and demonstrate that the stabilized metal compositions of this invention do not stain or discolor the gauze pad.

TABLE 2

| Staining Ability | | | | |
| --- | --- | --- | --- | --- |
| | Cation:Anion | Period of Exposure | | |
| Composition | Ratio | 1 HR | 24 HR | 72 HR |
| Example 1 (Cl) | 1:18 | = | = | = |
| Example 3 (Br) | 1:9 | = | = | = |
| Example 2a | 1:0 | +/− | ++ | ++ |

(++) indicates staining;
(=) indicates no staining

EXAMPLE 6 Antimicrobial Efficacy

In vitro tube susceptibility tests demonstrating the efficacy of the antimicrobial composition of this invention were performed. Silver Composition 1 was evaluated for antimicrobial efficacy and compared to equivalent concentrations of silver sulfadiazine (SSD) and silver nitrate. Organisms from clinical isolates from burn wound patients at the University of Wisconsin Hospital were used.

Background

Susceptibility to SSD is defined as inhibition of an organism at a concentration of 100 μg/ml. This is comparable to 0.28 μeq/ml of silver. For standardization of concentration, all antimicrobial solutions were calculated in μeq/ml. Ranges from 0.56 to 0.018 μeq/ml were tested.

Procedure

Bacterial suspensions of each isolate were prepared from log phase growth to approximate $10^6$ colony forming units per milliliter ("cfu/ml"). Each tube dilution of antimicrobial was inoculated with bacteria to a final concentration of $10^5$ cfu/ml. Tubes were incubated 24 hours at 35° C. and read for turbidity.

Bacteriocidal action (all microorganisms killed) was determined by performing growth subcultures from all tubes showing any inhibition of growth. Plates were incubated 24 hours at 35° C. and read for growth.

The lowest dilution showing growth inhibition (lack of turbidity) is the minimum inhibitory concentration (MIC). The lowest concentration showing no growth on additional plate subculture is the minimum bacteriocidal concentration (MBC). MIC and MBC results can differ +/−one dilution when tested and are still considered comparable.

Summary

Tables 3 and 4 summarize the results of the antimicrobial efficacy experiments. The MIC results for Silver Composition 1 was comparable to both the silver nitrate and the silver sulfadiazine controls. With regard to MBC results, Silver Composition 1 was comparable to silver nitrate (AgNO$_3$) solution for all isolates tested. Only one isolate showed a discrepancy with Silver Composition 1 and SSD on MBC results. Isolate #13, a coagulase negative Staphylococcus, had a significantly higher MBC with SSD than with Silver Composition 1 (or AgNO$_3$). The results of this experiment demonstrate that the metal-based antimicrobial compositions of this invention are effective against a broad spectrum of microbes.

TABLE 3

Minimum Inhibitory Concentrations*

| Organism | Minimum Inhibitory Concentration | | |
|---|---|---|---|
| | Ag Comp. 1 | AgNO$_3$ | SSD |
| 1. E. coli (A) | .035* | .035 | .070 |
| 2. E. coli (B) | .070 | .070 | .070 |
| 3. Ent. aerogenes | .035 | .035 | .070 |
| 4. Ent. cloacae | .070 | .070 | .070 |
| 5. Kl. pneumoniae | .070 | .070 | .070 |
| 6. Ps. aeruginosa | .070 | .035 | .070 |
| 7. S. aureus (A) | .140 | .140 | .280 |
| 8. S. aureus (B) | .070 | .070 | .140 |
| 9. S. aureus (C) | .070 | .140 | .140 |
| 10. S. aureus (D) | .035 | .035 | .035 |
| 11. S. aureus (E) | .070 | .140 | .070 |
| 12. S. aureus (F) | .280 | .140 | .140 |
| 13. Staph., coag. neg. | .035 | .035 | .035 |
| 14. Enterococcus | .140 | .140 | .140 |
| 15. Candida | .280 | .280 | .280 |

TABLE 4

Minimum Bacteriocidal Concentration*

| Organism | Minimum Bacteriocidal Concentration | | |
|---|---|---|---|
| | Ag Comp. 1 | AgNO$^3$ | SSD |
| 1. E. coli (A) | .070 | .035 | .140 |
| 2. E. coli (B) | .070 | .070 | .140 |
| 3. Ent. aerogenes | .035 | .070 | .070 |
| 4. Ent. cloacae | .070 | .140 | .280 |
| 5. Kl. pneumoniae | .140 | .070 | .070 |
| 6. Ps. aeruginosa | .140 | .280 | .140 |
| 7. S. aureus (A) | .280 | >.560 | .560 |
| 8. S. aureus (B) | .280 | .560 | >.560 |
| 9. S. aureus (C) | .140 | .140 | .280 |
| 10. S. aureus (D) | .070 | .070 | .140 |
| 11. S. aureus (E) | .140 | .280 | .280 |
| 12. S. aureus (F) | .560 | .560 | .280 |
| 13. Staph., coag. neg. | .070 | .140 | .560 |
| 14. Enterococcus | .140 | .140 | .280 |
| 15. Candida | .280 | .560 | .280 |

*For Table 3 and Table 4 the numbers in the columns represent the concentration of silver ions in the broth with units of microequivalents per ml of broth (μeq/ml).

EXAMPLE 7 Stable Silver-Based Antimicrobial Cream

To illustrate another form of the composition of this invention, an antimicrobial silver-based cream composition was made. This composition was solid at room temperature, photostable and non-staining and is useful in topical applications for the prevention and treatment of a wide variety of dermal infections. The antimicrobial silver-based cream composition was made by heating to 50° C., 5 grams of the liquid Silver Composition 1 and slowly stirring in 5 grams of polyethylene glycol having an average molecular weight of 3,500. The mixture was stirred until all of the high molecular weight PEG was melted. The solution, while being stirred, was allowed to cool to room temperature. The final form of the composition was a cream that was photostable and had good antimicrobial efficacy.

EXAMPLE 8 Treatment of Absorptive Medical Devices

To illustrate that the compositions of this invention are useful in rendering medical devices infection resistant, medical devices comprised of absorptive material and lipophilic polymers were treated and tested for photostability and antimicrobial efficacy. Silver Composition 1 was used to treat cotton gauze. Specifically, the composition was poured onto a 2×2 inch piece of medical cotton gauze where it remained for less than 1 minute to allow absorption of the metal composition into the gauze. After the time for absorption had elapsed, the excess metal composition was wrung out of the treated gauze. As a control, a cotton gauze was treated with an aqueous silver nitrate solution (at the equivalent silver ion concentration as Silver Composition 1). Both the treated gauze and the control gauze were then placed a distance 6 inches from the plant growth light for up to 72 hours. To test antimicrobial efficacy, the treated gauze was placed on a petri dish containing culture medium that had previously been plated with a bacterial suspension and incubated overnight. The next day, the zone of growth inhibition was measured. For comparison, an untreated cotton gauze was tested using the same antimicrobial procedures.

Results

The gauze that had been treated with Silver Composition 1 showed no discoloration on exposure to the light after 72 hours. In comparison, the cotton gauze treated with the silver nitrate solution showed discoloration after 4 hours of light exposure and marked discoloration after 72 hours of growth light exposure. The treated cotton gauze showed good zones of inhibition for all bacterial challenges. The untreated gauze showed no zones of inhibition. These results demonstrate that the treatment of absorptive medical devices using the metal compositions of this invention will provide infection resistance while being photostable.

EXAMPLE 9 Treatment of Polyurethane Catheters

To demonstrate the utility in making catheters infection resistant using the stabilized silver-based compositions of this invention, a number of studies were performed on catheters treated with Silver Composition 1. The treated catheters were then exposed to a broad spectrum of microbes to study their infection resistance.

Two inch long test catheter segments made of polyurethane (Estane from BF Goodrich) were treated by submersing the test catheter segments in Silver Composition 1 for 24 hours. After removal from the Silver Composition 1 solution, the excess solution was wiped off the outside of the catheter using paper towels and removed from the inner lumen by flushing with a stream of air.

The treated test catheter samples had an approximately 5% increase in size and a softer feel (lower durometer) than the untreated catheters. This indicated that Silver Composition 1 was absorbed into the polyurethane matrix of the catheter.

Bacterial solutions were made of various ATCC organisms and clinical isolates to challenge the treated (test) catheters. Treated and untreated catheters (controls) were exposed to the bacterial solutions by flowing the viable organisms through the inner lumen. Inoculum for each catheter was approximately $10^6$ organisms (range $5.6 \times 10^5$ to $1.2 \times 10^6$). Catheter segments were then incubated to allow the individual bacteria time to establish surface colonization. To determine surface colonization, the inner lumen was subsequently washed with sterile broth to retrieve any viable organisms present, and the washings were then cultured by plating onto blood agar. Plates were incubated overnight and read for numbers of bacteria colonies recovered. Colony counts from the plates of treated catheters were compared with colony counts from the plates of untreated catheters to determine the effectiveness of the treatment.

Results

Table 5 shows the results of the above study. The results indicate that Silver Composition 1 confers antimicrobial properties to treated catheters. For each of the bacteria species used, there appeared to be no bacterial colonization of the polymer surface as determined by the number of viable organisms retrieved in the treated catheter, even with the high inoculation numbers used. In contrast, the untreated catheters showed no inhibition of the same organisms, as can be seen by the confluence (heavy overgrowth) on the culture plates. These results indicate that catheters treated with silver-based compositions of the invention were infection resistant.

TABLE 5

Infection Resistance of Treated Polyurethane Catheters

| ATCC Organisms | Treated Catheter+ | Control Catheter |
|---|---|---|
| Staphylococcus aureus | 0 | *TNTC |
| Staphylococcus epidermidis | 0 | *TNTC |
| Streptococcus pyogenes | 0 | *TNTC |
| Escherichia coli | 0 | *TNTC |
| Pseudomonas aeruginosa | 0 | *TNTC |
| Enterobacter cloacae | 0 | *TNTC |
| Klebsiella pneumoniae | 0 | *TNTC |
| Serratia marcescens | 0 | *TNTC |
| Proteus vulgaris | 0 | *TNTC |

+ numbers in column indicate number of organisms recovered.
TNTC = colonies present are in numbers Too Numerous To Count.
*Represents confluent growth.

EXAMPLE 10 Treatment Times

The following illustrates that infection resistance can be conferred to catheters treated with the composition of the invention. Polyurethane catheter segments were treated as described in Example 9 except that treatment times were for 15, 30 and 45 minutes. The treated catheters were challenged with four of the ATCC organisms previously demonstrating susceptibility. Untreated catheter segments were also tested as a control.

Results

Table 6 summarizes the results of the antimicrobial challenge. The results demonstrate that catheter segments treated with Silver Composition 1 were resistant to infection against each of the bacteria that were used as a challenge. There appears to be minimal, if any, colonization or viable organisms present on the inner lumen of the treated catheters when the exposure time to the polymer was decreased to as low as 15 minutes. In contrast, untreated catheters showed no inhibition of the same organisms, as demonstrated by the heavy overgrowth on the culture plates. This study illustrates that the optimal treatment time for a medical device has to be empirically derived in the industrial setting.

TABLE 6

Treatment Time

| | | Test exposure time+ (in minutes) | | |
|---|---|---|---|---|
| Test (ATCC) Organism | Control | 15 | 30 | 45 |
| Staph. aureus | TNTC | 2 | 1 | 41 |
| Staph. epidermidis | TNTC | 0 | 5 | 15 |
| Escherichia coli | TNTC | 0 | 0 | 0 |
| Strep. Pyogenes | 234 | 0 | 0 | 0 |

+ numbers in column indicate number or organisms recovered.
TNTC = colonies present are in numbers Too Numerous To Count.

EXAMPLE 11 Effect of Washing on Treated Catheters

As discussed above, it is believed that the metal-based compositions of this invention are absorbed into the polymer material and are not just coated on a surface. Catheters treated with Silver Composition 1 show an increase in size and have a lower durometer (i.e. feel softer). These observations imply that the polymer material is absorbing Silver Composition 1 into the polymer matrix. To further demonstrate that Silver Composition 1 is not just surface coating, but uses the polymer matrix as a reservoir for the metal based composition, the treated catheters were washed to remove residual surface composition from the catheters' surfaces.

Catheters treated with the Silver Composition 1, as described in Example 9 were immersed in 0.9% saline bath, for 24 hours. After soaking in the saline bath, the treated catheters were further rinsed under a running stream of distilled water. After being air dried, the catheters were challenged with various ATCC microbes, according to the procedures outlined in Example 9.

Results

Table 7 summarizes the results of this study. Catheters treated with the Silver Composition 1 show only a minimal loss of efficacy following the washing procedure. Treated catheters still maintained antimicrobial inhibitory action against large numbers ($10^6$ cfu) of organisms. Control catheters (untreated catheters) showed substantial growth for all the organisms. These results indicate that Silver Composition 1 uses the polymer matrix as a reservoir for the silver based composition. If Silver Composition 1, which is very water soluble, is only a surface treatment, one would expect a much higher number of organisms, similar to the numbers recovered from the control catheters, to be recovered. On the contrary, only a small number of organisms were recovered in comparison to the untreated catheters.

TABLE 7

Effect of Washing Treated Catheters

| ATCC Organisms | Treated Catheter+ | Control Catheter |
|---|---|---|
| Staphylococcus aureus | 163+ | *TNTC |
| Staphylococcus epidermidis | 189 | *TNTC |
| Streptococcus pyogenes | 140 | *TNTC |
| Escherichia coli | 0 | *TNTC |
| Pseudomonas aeruginosa | 0 | *TNTC |
| Enterobacter cloacae | 0 | *TNTC |
| Klebsiella pneumoniae | 30 | *TNTC |
| Serratia marcescens | 0 | *TNTC |
| Proteus vulgaris | 21 | *TNTC |

+ numbers in column indicate number of organisms recovered.
TNTC = colonies present are in numbers Too Numerous To Count.
*Represents confluent growth.

EXAMPLE 12 Effects of Repeated Antimicrobial Challenges

To demonstrate that the antimicrobial metal compositions of this invention provide long lasting infection resistance to the polymer surface of medical devices, catheters having been treated once were challenged repeatedly without any additional treatment. As in Example 9, treated and untreated catheters were exposed to various bacterial solutions by flowing viable organisms through the inner lumen. Inoculum for each catheter had approximately $5.0 \times 10^3$ organisms. Catheter segments were then incubated to allow the individual bacteria to colonize the surface of the polymer material. To determine colonization, the inner lumens were subsequently washed with sterile broth to retrieve viable organisms, and the washings were then cultured by plating onto blood agar. Plates were incubated overnight and read for numbers of bacteria recovered. Counts from the plates were compared to determine the effectiveness of the polymer treatment. This procedure constituted challenge No. 1. The entire procedure was then repeated in challenge No. 2, and again a third time in challenge No. 3. Catheters were not sterilized, washed, or again exposed to the Silver Composition 1 between challenges.

Results

Table 8 summarizes the results from this study. The antimicrobial coating appears to bestow sufficient protection to the catheters that subsequent microbial challenges are still inhibited. These results illustrate that the protective coating is long lasting.

TABLE 8

Effects of Repeated Antimicrobial Challenges

| ATCC Organism+ | Challenge #1 | | Challenge #2 | | Challenge #3 | |
|---|---|---|---|---|---|---|
| | test | control | test | control | test | control |
| S. marcescens | 0 | *TNTC | 0 | TNTC | 0 | *TNTC |
| P. vulgaris | 0 | TNTC | 0 | *TNTC | 0 | *TNTC |

+ numbers in column indicate number of organisms recovered.
TNTC = colonies present are in numbers Too Numerous To Count
*Represents confluent growth EXAMPLE 13 Light Stability A problem with many of the current approaches of making infection-resistant polymers using silver metal ions is that the treatments are not photostable. That is to say, after treatment, the medical device needs to be protected from light. In light, silver ions are reduced to metallic silver which has poor antimicrobial efficacy. Furthermore, from an aesthetic viewpoint, catheters are less than optimal when they change from their original color to a dark color. As a result of photoinstability, special handling and packaging are required for medical devices treated using methods described in the prior art. To demonstrate that polymers treated with the antimicrobial silver compositions of this invention are photostable, treated catheters from Example 9 were exposed to the plant growth light for 72 hours. Both untreated catheters and catheters treated in the same fashion as described in Example 9 but with an equivalent concentration of silver nitrate in water, were used as controls.

Results

The catheters treated with Silver Composition 1 showed no discoloration in comparison to untreated catheters after 72 hours. In fact, the treated catheters showed no discoloration when exposed to sunlight for longer than 1 month. In contrast, catheters that had been exposed to the silver nitrate solution began to discolor within 1 hour. After 72 hours, the silver nitrate control catheters showed marked darkening in comparison to the untreated catheters and the catheters treated with Silver Composition 1. This study demonstrates that polymers that are made infection-resistant using the metal compositions of this invention are indeed stable.

EXAMPLE 14 Treatment of Other Polymer Materials

To further illustrate the utility of the metal compositions of this invention in rendering polymers infection resistant, the study described in Example 9 was repeated using polyethylene tubing (from Intramedic) and white silicone radiopaque tubing (from Cook Catheter). The results of this study are shown in Table 9. The treated catheters showed some recovery of bacterial colonies in the S. aureus and S. epidermidis challenges. However, in comparison to the untreated catheters, the treatment of the catheter materials with Silver Composition 1 provided marked infection resistance to the polymer materials. It should be noted that treated catheters showed no discoloration over long periods of time when left exposed to sunlight. This further demonstrates the stability of the metal compositions of this invention.

TABLE 9

Treatment of Polyethylene and Silicone+

| Organism | Polyethylene | | Silicone | |
|---|---|---|---|---|
| | test | control | test | control |
| S. aureus | 205 | *TNTC | 84 | TNTC |
| S. epidermidis | 58 | TNTC | 55 | TNTC |
| E. coli | 0 | *TNTC | 0 | 147 |

+ numbers in column indicate number of organisms recovered.
TNTC = colonies present are in numbers Too Numerous To Count
*Represents confluent growth

EXAMPLE 15 Comparative Tests

Several studies were conducted in order to evaluate the efficacy of the various methods taught by Romans, U.S. Pat. No. 3,092,552 ('552).

Study No. 1

At column 7, lines 36–50, the '552 patent, teaches that one can effectively treat cellophane or other materials by dipping them into an aqueous solution containing 0.03% to 0.05% silver nitrate, then into a solution containing 15% glycerine and 0.03% to 0.05% sodium chloride or cupric chloride. It is alleged that the chlorides stabilize the oligodynamic silver and tend to prevent discoloration.

The following study was performed to evaluate these teachings:

1. A 0.05% silver nitrate solution in water and a 15% aqueous glycerine solution containing 0.05% sodium chloride were made.

2. A 2×2 inch cotton gauze was dipped into the silver nitrate solution and wrung out and then dipped into the glycerine/sodium chloride solution and wrung out. As a control, another 2×2 inch cotton gauze was treated in a similar fashion with the silver nitrate solution but was not treated with the glycerine/sodium chloride solution.

3. Both treated gauzes, along with a gauze with no treatment, were then placed 6" under the plant growth light which simulates sunlight. The time it took to discolor was noted for the treated pads.

Both the cotton gauze treated with the silver nitrate solution followed by the glycerine/sodium chloride solution, and the cotton gauze treated with only the silver nitrate solution began to discolor within five minutes of exposure to the plant growth light. After 30 minutes, both treated gauzes showed marked discoloration. No difference in rate of discoloration was noted.

Study No. 2

At column 6, lines 4 through 16, the '552 patent discloses the immersion of a surgical gauze in a 0.1% aqueous solution of Stock Solution A for two minutes, passing it through a wringer, and then treating the gauze with a 0.2% solution of cupric chloride or sodium chloride. It asserts that gauze so treated is antiseptic and can be exposed to sunlight and placed in an autoclave for thirty minutes at twenty pounds pressure, without affecting its germicidal activity or coloration.

The following study evaluates the above protocol:

1. Stock Solution A was made as taught the '552 patent, at column 2, lines 37–43. Silver nitrate (1.4 g), dextrose (1.4 g) and cupric nitrate (1.4 g), were all dissolved in 10 ml of water containing 0.1 ml of nitric acid. The solution was stirred until all solids were dissolved. The appearance of Stock Solution A was that of a clear, bright blue solution with no precipitate.

2. A 0.1% aqueous solution of Stock Solution A and a 0.2% sodium chloride solution were then made.

3. Three other Stock solutions were made for test comparison. The formulations of these other Stock Solutions are as follows:

| Ingredient | Stock Solution B | Stock Solution C | Stock Solution D |
|---|---|---|---|
| Silver Nitrate | 1.4 g | 1.4 g | 1.4 g |
| Dextrose | 0 g | 1.4 g | 1.4 g |
| Cupric Nitrate | 0 g | 0 g | 0 g |
| Zinc Nitrate | 0 g | 0 g | 1.4 g |
| Nitric Acid | 0 ml | 0 ml | 0.2 ml |
| Water | 10 ml | 0 ml | 10.0 ml |

4. A 0.1% soaking solution for each of the above stock solutions was made.

5. A 2×2 inch cotton gauze was soaked for two minutes in each of the soaking solutions, wrung out, and then soaked in a 0.2% sodium chloride solution. (Test Gauze). As controls, cotton gauzes were similarly treated with the soaking solutions and wrung out. But instead of soaking them in a sodium chloride solution, each control gauze was soaked in a water bath with no other salts added.

6. Both the test and control gauzes were then placed under the plant growth light and the discoloration of the gauze over time was noted.

7. For comparison, a cotton gauze treated with Silver Composition 1 was also exposed to the plant growth light.

Table 11 shows the results of this experiment. The cotton gauze treated with a solution made from Stock Solution A followed by the sodium chloride solution had the highest light resistance of all gauzes tested. The gauze treated only with the solution made from Stock Solution A showed no better light stability then the other treated gauzes. Although cotton gauze treated as described in the '552 patent appears to have improved light resistance, such treatment does not appear to provide long term or permanent light stability.

For all other samples treated with the different stock solutions, there was no difference between the gauzes treated with both the stock solutions followed by a sodium chloride solution or treated only with the stock solution. It appears That the only time sodium chloride treatment improves light stability is when the stock solution contains cupric nitrate.

In contrast, cotton gauze treated with the stabilized stock solution of the present invention, Silver Composition 1 ("SC1"), shows no discoloration under similar circumstances.

TABLE 11

Light Stability of Treated Cotton Gauzes

| Solution | Time (Minutes) | | | | | | |
|---|---|---|---|---|---|---|---|
| | 0 | 10 | 25 | 40 | 60 | 180 | 21 hrs |
| A | − | − | − | + | ++ | ++ | +++ |
| Control A | − | ++ | +++ | +++ | +++ | +++ | ++++ |
| B | − | +++ | +++ | +++ | x | x | ++++ |
| Control B | − | +++ | +++ | +++ | x | x | ++++ |
| C | − | +++ | +++ | +++ | x | x | ++++ |

TABLE 11-continued

Light Stability of Treated Cotton Gauzes

| Solution | Time (Minutes) | | | | | | |
|---|---|---|---|---|---|---|---|
| | 0 | 10 | 25 | 40 | 60 | 180 | 21 hrs |
| Control C | – | +++ | +++ | +++ | x | x | ++++ |
| D | – | ++ | +++ | x | +++ | x | ++++ |
| Control D | – | ++ | +++ | x | +++ | x | ++++ |
| SC1 | – | – | – | – | – | – | – |
| Untreated Gauze | – | – | – | – | – | – | – |

+ indicates discoloration. Multiple "+" indicates increased discoloration. "–" indicates no discoloration. "x" indicates no observations recorded.

Study No. 3

At column 4, lines 21–52, the '552 patent discloses an ointment comprised of the following:

| | Percent |
|---|---|
| Silver nitrate | 1.0 |
| "Carbowax 4000" | 55.0 |
| Polyethylene glycol (m.w. 300) | 18.0 |
| "Carbowax 1500" | 5.0 |
| Corn Starch, USP 0 | .2 |
| Cupric nitrate (purified) | 0.2 |
| Sodium Chloride, C.P. | 1.0 |
| Lanolin anhydrous | 8.0 |
| Beeswax | 2.0 |
| Distilled water | 12.6 |

At column 4, line 74—column 5, line 10, the '552 patent further teaches that a small amount of an ion other than silver added to the mixture increases oligodynamic activity. It states that as little as 0.01% sodium chloride increases the solubility of silver probably by the formation of complex silver salts such as $NaAgCl_2$.

A study was performed according to the above protocol. A composition was made similar to the one described above except that polyethylene glycol (m.w.3,400) was used instead of Carbowax 4000 and polyethylene glycol (m.w. 1,500) was used instead of Carbowax 1,500.

Besides making a silver composition as described in the '552 patent (Composition B), three other compositions were made. Composition A contained the same ingredients as in Composition B but without the use of silver. This composition serves as a control on light stability for comparison with compositions that contain silver. In Composition C, sodium chloride was left out. The purpose of using this composition was to determine whether compositions with sodium chloride are more lightstable than compositions without sodium chloride. In Composition D, cupric nitrate was left out. Again, this composition was included to evaluate the importance of the addition of the copper ion. The study was performed as follows:

1. Compositions A–D were made in accordance with the teachings in the '552 patent. The percentages of ingredients are as follows:

| | A | B | C | D |
|---|---|---|---|---|
| Silver nitrate | 0 | 1.0 | 1.0 | 1.0 |
| PEG (m.w. 3,400) | 55.0 | 55.0 | 55.0 | 55.0 |
| Polyethylene glycol (m.w. 300) | 18.0 | 18.0 | 18.0 | 18.0 |
| PEG (m.w. 1,500) | 5.0 | 5.0 | 5.0 | 5.0 |
| Corn Starch | .2 | .2 | .2 | .2 |
| Cupric nitrate (purified) | 0.2 | 0.2 | 0.2 | 0 |
| Sodium Chloride, C.P. | 1.0 | 1.0 | 0 | 1.0 |
| Lanolin anhydrous | 8.0 | 8.0 | 8.0 | 8.0 |
| Beeswax | 2.0 | 2.0 | 2.0 | 2.0 |
| Distilled water | 12.6 | 12.6 | 12.6 | 12.6 |

The appearances of the final compositions are as follows:
Composition A: Bright, milky, yellow, creamy solid.
Composition B: Bright, milky, yellow, creamy solid.
Composition C: Light, blue-green, creamy solid.
Composition D: White, creamy solid.
All compositions were stored in the dark until testing.

2. Light stability of these final compositions was determined by applying a thin film-like sample of each to a paper liner and placing these samples under the plant growth light. The discoloration over time was noted. Similar samples serving as controls were applied to a paper liner but kept in the dark. A sample of the stabilized silver of the present invention according to Example 6 was also tested as a control.

The results of the light stability of Compositions A–D and the present invention's stabilized silver composition are presented in Table 12. All the compositions except the one of the present invention changed color when exposed to the plant growth light. Compositions A–D were not photostable. Composition A (containing no silver) changed from a bright, milky yellow to a white composition after 16 hours of light exposure. Composition B, the composition described in the '552 patent, changed color almost immediately. It turned from its original bright yellow color to a dark-grayish brown color. The color deepened over time. Composition C (containing no sodium chloride) was the most stable of compositions B–D containing silver. However, after 16 hours, it changed from a bluish-green color to a dark, brownish gray color. Finally, Composition D, containing no cupric nitrate, discolored almost immediately. The composition turned from its white milky appearance to a dark bluish gray appearance. The stabilized silver composition of the present invention did not discolor.

TABLE 12

Light Stability of Compositions A–D

| Sample | 0 | 5 | 8 | 15 | 35 | 16 hrs |
|---|---|---|---|---|---|---|
| Composition A | – | – | + | – | – | +++ |

TABLE 12-continued

| Sample | Light Stability of Compositions A–D | | | | | |
|---|---|---|---|---|---|---|
| | 0 | 5 | 8 | 15 | 35 | 16 hrs |
| Composition B | − | +++ | ++++ | ++++ | ++++ | ++++ |
| Composition C | − | − | ++ | − | − | ++++ |
| Composition D | − | +++ | ++++ | ++++ | ++++ | ++++ |
| present invention | − | − | − | − | − | − |

"+" indicates discoloration. Multiple "+" indicates increased discoloration. "−" indicates no discoloration.

It appears that the antiseptic ointment composition based on the '552 patent disclosure is not light-stable. The use of sodium chloride in the composition seems to destabilize the silver, as seen by comparing Composition B with Composition C. Cupric nitrate appears to stabilize the silver against discoloring, but it does not prevent the composition from discoloring over time. In comparison, the stabilized silver compositions of the present invention are light stable. No change in appearance is noted after long periods of light exposure.

EXAMPLE 16 Antimicrobial Adhesives

Antimicrobial dressings were made by taking 100 grams of a polyurethane adhesive with a large percentage of the soft segments of the polyurethane adhesive made up of polyethylene glycol, e.g., a polyurethane according to Example 1 of U.S. patent application Ser. No. 07/365,313, and thoroughly stirring in 1.4 ml of an aqueous 0.1 meq/ml silver nitrate solution followed by 1.4 ml of an aqueous 1 meq/ml sodium chloride solution. The adhesive solution remained clear with no precipitate. This stabilized silver-containing adhesive solution was then coated to a 1.2 mil thickness on a 1.0 mil thick polyurethane film and dried at 50° C. for 10 minutes. The film with the adhesive on it was clear, had tack and was photostable.

The antimicrobial dressing was tested for bacterial growth inhibition by the following standard procedures. Bacterial suspensions ($10^5$ cfu/ml) were plated on culture media in petri dishes. Several 1 sq cm sections of dressings were placed on the inoculated culture media and incubated overnight. The size of the zone of growth inhibition in millimeters was recorded. As a control, thin film dressings without any stabilized silver treatment were tested.

The results of the experiment are shown in Table 13. All dressings containing stabilized silver demonstrated excellent growth inhibition against all bacteria. None of the control dressings showed any zone of growth inhibition.

TABLE 13

Stabilized Silver Adhesive Antimicrobial Spectrum

| Organism | Zone of Inhibition* |
|---|---|
| Staphylococcus aureus | 18 |
| Staphylococcus epidermidis | 18 |
| Streptococcus pyogenes | 14 |
| Cocherichia coli | 17 |
| Enterbacter cloacae | 16 |
| Klebsiella pneumoniae | 15 |
| Proteus vulgaris | 15 |
| Serratia marcescens | 17 |
| Pseudomoeas seruginosa | 16 |

*zones in mm using 10 mm disc

EXAMPLE 17 Stable Silver-Based Foam

To further illustrate another form of this invention, a photostable silver-based polyurethane foam was made. The silver-based polyurethane foam was made using a foamable hydrophilic polyurethane prepolymer that, when mixed with silver nitrate and sodium chloride water solutions, reacts to form carbon dioxide and a silver-based hydrophilic polyurethane foam polymer. The polyurethane prepolymer consists of an acyclic polyether, terminated with an isocyanate.

The photostable silver-based foam was made by taking 22.3 grams of a polyurethane prepolymer (Hypol 2002, W.R. Grace & Co.) and quickly stirring thoroughly in 0.62 ml of a 1 meq/ml of silver nitrate dissolved in water and then immediately stirring thoroughly in 22 ml of a 2.5 meq/ml of sodium chloride dissolved in the water (the ratio of chloride anions to silver cations was 88 to 1). The mixture was stirred for approximately 30 seconds. The mixture immediately began to react to form a foam. After 15 minutes, the foam was removed from its container and stored overnight in the dark to allow the foam to dry. A sample of the silver-based foam was exposed to a plant growth light for more than 24 hours with no signs of discoloration. Similar foams have been made that have demonstrated light stability for greater than 2 months. (Note: The 'two month' period represents the time spent from when the composition was made to the present. There is no indication that the composition will begin to discolor. Therefore, this composition has indefinite photostability.) This silver-based foam can be used for a large variety of medical applications, including an antimicrobial absorptive foam dressing.

EXAMPLE 18 Unstable Silver-Based Foam

For the purpose of illustrating the importance of using an excess amount of halide in the silver-based foam composition to provide photostability, a silver-based foam was made using no sodium chloride. This silver-based foam was made by taking 11.1 grams of a polyurethane prepolymer (Hypol 2002, W.R. Grace & Co.) and quickly stirring thoroughly in 0.31 ml of a 1 meq/ml of silver nitrate dissolved in water and then immediately stirring thoroughly in 22 ml of water (the ratio of chloride anions to silver cations was 0 to 1). The mixture was stirred for approximately 30 seconds. The mixture immediately began to react to form a foam. After 15 minutes, the foam was removed from its container and stored overnight in the dark to allow the foam to dry. A sample of the silver-based foam was exposed to a plant growth light. After only 15 minutes, this foam sample changed from a white color to a dark brown color. A sample of the silver-based foam also discolored in ambient room light after only 30 minutes. This example demonstrates that without the use of an excess of chloride anions in the composition, the silver-based foam is highly photo-instable.

EXAMPLE 19 Unstable Silver-Based Foam

To yet further illustrate the importance of using an excess amount of halide in the silver-based foam composition to provide photostability, a silver based foam was made using sodium chloride in an equivalent amount to silver nitrate. This silver-based foam was made by taking 13.4 grams of a polyurethane prepolymer (Hypol 2002, W.R. Grace & Co.) and quickly stirring thoroughly in 0.372 ml of a 1 meq/ml of silver nitrate dissolved in water and immediately stirring thoroughly in 0.144 ml of a 2.5 meq/ml of sodium chloride dissolved in water that had been previously mixed with 13 ml of water (the ratio of chloride anions to silver cations was 1 to 1). The mixture was stirred for approximately 30 seconds. The mixture immediately began to react to form a foam. After 15 minutes, the foam was removed from its container and stored overnight in the dark to allow the foam to dry. A sample of the silver-based foam was exposed to a plant growth light. As with Additional Example 8, after only 15 minutes, this foam sample changed from a white color to a dark brown color. A sample of the silver-based foam also discolored in ambient room light after only 30 minutes. It should be noted that the rate and degree of color change in Example 9 was equivalent to the rate and degree of color change noted in Example 8. Again, this example demonstrates that without the use of an excess amount of chloride anions in the composition, the silver-based foam is highly photo-instable. This example further illustrates that simply adding an equivalent amount of chloride anion to the silver composition does not provide any added photostability over a silver composition without the added chloride anion.

EXAMPLE 20 Stable Silver-Based Foam

To demonstrate the method for the direct incorporation of silver-based compositions to make a photostable silver-based polyurethane foam, a silver composition was made by taking 100 grams of polyethylene glycol (75% 600 molecular weight and 25% 1000 molecular weight) and was mixed with 0.58 ml of a 5 meq/ml solution of silver nitrate dissolved in water and 12.5 ml of a 4 meq/ml solution of sodium chloride and 6.25 ml of water. The mixture was stirred producing a clear solution with no precipitate. 6.7 grams of this silver composition and 10 grams of water were added to 10 grams of a polyurethane prepolymer (Hypol, Hampshire Chemical Corporation) and stirred for approximately 30 seconds. The mixture immediately began to foam. After 15 minutes, the foam was removed from its container and stored overnight in the dark to allow the foam to dry. A sample of the silver-based foam was exposed to a plant growth light for more than 24 hours with no signs of discoloration. Similar foams have been made that have demonstrated light stability for greater than 6 months. (Note: The "six month" period represents the time from when the composition was made to the present. There is no indication that the composition will begin to discolor. Therefore, this composition has indefinite photostability.) This silver-based foam can be used for a large variety of medical applications, including as an antimicrobial absorptive foam dressing.

EXAMPLE 21 Stable Silver-Based Solution Using Nonoxynol

To illustrate the use of a polyethylene glycol conjugate as the acyclic ether in the present invention, a photostable silver-based composition was made using nonoxynol. Merck Index (6518, 10th Edition) describes nonoxynol as a polyethyleneglycol mono(nonylphenyl) ether sold under a variety of trade names including lgepal CO-630 and Nonoxynol-9. Nonoxynol is typically prepared by reacting nonylphenol with ethylene oxide to produce the compound which has an average of 9 ethylene oxide units per molecule. Nonoxynol-9 is currently widely used in birth control as a spermatocide.

The composition was made by stirring 21.1 grams of Igepal CO-630 (from Rhone-Poulenc, Inc.) and adding 0.1 ml of a 1 meq/ml of silver nitrate dissolved in water followed by 1 ml of a 4 meq/ml of sodium chloride dissolved in water. After stirring for 1 hour, a photostable translucent solution was formed. The ratio of chloride anions to silver cations was 40 to 1. A sample of this solution exposed to a plant growth light for over 24 hours showed no signs of discoloration. No precipitate was noted upon microscopic examination of this composition. This silver-based composition has potential use as an antimicrobial spermatocide for use in birth control devices.

EXAMPLE 22 Unstable Silver-Based Solution Using Nonoxynol

To further illustrate the need for the use of an excess amount of halide, a silver-based composition was made using nonoxynol that only used sodium chloride in an equivalent amount to silver nitrate. The composition was made by stirring 21.1 grams of lgepal CO-630 (from Rhone-Poulenc, Inc.) and adding 0.1 ml of a 1 meq/ml of silver nitrate dissolved in water followed by 0.025 ml of a 4 meq/ml of sodium chloride dissolved in water. After stirring for 1 hour, a translucent solution with a yellowish tinge was formed. The ratio of chloride anions to silver cations was 1 to 1. A sample of this solution was exposed to a plant growth light. After only 15 minutes of exposure, the sample had marked discoloration (to a salmon-orange color). A fine particulate precipitate was noted upon microscopic examination of this composition. This silver-based composition further demonstrates that chloride anion in an equivalent amount to silver cation does not photostabilize the silver.

EXAMPLE 23 Stable Silver-Based Solution Using Poloxamers

To illustrate the use of a polyethylene glycol block copolymer as the acyclic ether in the present invention, a photostable silver-based composition was made using a poloxamer. Merck Index (7432, 10th Edition) describes poloxamers as polyethylenepolypropylene glycol block copolymers. The poloxamers are typically used as surfactants and sold under the trade name of Pluronics (BASF).

To further illustrate the present invention, a photostable silver-based composition was made using a Pluronic 10R5—a poloxamer with the basic block copolymer structure of Polypropyleneglycol:Polyethyleneglycol:Polypropyle neglycol. The composition was made by stirring 9.9 grams of Pluronic 10R5 and adding 0.05 ml of a 1 meq/ml of silver nitrate dissolved in water followed by 0.2 ml of a 4 meq/ml of sodium chloride dissolved in water and 0.6 ml of water. After stirring for 1 hour, a photostable solution was formed. The ratio of chloride anions to silver cations was 16 to 1. A sample of this solution exposed to a plant growth light for over 24 hours showed no signs of discoloration. No precipitate was noted upon microscopic examination of this composition. This silver-based composition has potential use as an silver-based antimicrobial surfactant.

EXAMPLE 24 Unstable Silver-Based Solution Using Poloxamers

To yet further illustrate the need for the use of an excess amount of halide, a silver-based composition was made using a poloxamer, but only adding sodium chloride in an equivalent amount to the silver nitrate. The composition was made by stirring 9.9 grams of Pluronic 10R5 and adding 0.05 ml of a 1 meq/ml of silver nitrate dissolved in water followed by 0.0125 ml of a 4 meq/ml of sodium chloride dissolved in water and 0.6 ml of water. The composition was stirred for 1 hour. The ratio of chloride anions to silver cations was 1 to 1. A sample of this composition was exposed to a plant growth light. After only 15 minutes of exposure, the sample had marked discoloration (to a dark orange color). A sample of this composition stored in the dark began to discolor within 30 minutes. A fine particulate precipitate was noted upon microscopic examination of this composition. This silver-based composition demonstrates that chloride anion in an equivalent amount to silver cation does not photostabilize the silver.

EXAMPLE 25 Hydrophilic Stable Silver-Based Antimicrobial Cream/Ointments

To illustrate another hydrophilic cream/ointment form of this invention, a photostable silver-based cream composition was produced. This resulting silver composition was a photostable solid at room temperature. The silver-based cream composition was made by heating until melted 25 grams of a blend of polyethylene glycol consisting of the following:

|  | Percentage |
| --- | --- |
| Polyethylene Glycol 300 | 63% |
| Polyethylene Glycol 1000 | 5% |
| Polyethylene Glycol 3400 | 32% |

This blend of polyethylene glycols is similar to Solu-Base, a polyethylene glycol blend sold by Norwich-Eaton for wound care use.

Silver nitrate solution (0.675 ml of a 1 meq silver nitrate/ml) was added to the above melted blend of polyethylene glycols while being stirred, followed by the addition of a sodium chloride solution (3.825 ml of a 3 meq sodium chloride/ml). The mixture was stirred at 48° C. for 1 hour and then allowed to cool. Under ambient light conditions, no discoloration of this composition has occurred after a period of 2 years. (Note: The 'two year' period represents from the time when the composition was made to the present. There is no indication that the composition will be begin to discolor. Therefore, it is felt that this composition has indefinite photostability.) The composition was hydrophilic and water soluble.

EXAMPLE 26 Unstable Hydrophilic Silver-Based Antimicrobial Cream/Ointment

To illustrate the need for excess halide in a cream form of this invention, a silver-based cream composition equivalent to the composition in Example 24 was made but without the addition of sodium chloride. Like example 24, this composition was also a solid at room temperature, but this composition was photo-unstable. The silver-based cream composition was made by heating until melted 25 grams of a blend of polyethylene glycol consisting of the following:

|  | Percentage |
| --- | --- |
| Polyethylene Glycol 300 | 63% |
| Polyethylene Glycol 1000 | 5% |
| Polyethylene Glycol 3400 | 32% |

Silver nitrate solution (0.675 ml of a 1 meq silver nitrate/ml) was added to the above melted blend of polyethylene glycols while being stirred. The mixture was stirred at 48° C. for 1 hour and then allowed to cool. The initial appearance of the composition was yellow. A thin film of this composition was placed on a paper liner which began to discolor to a light gray color after 5 minutes under the plant growth light. After 30 minutes of additional exposure to the plant growth light, this composition darkened to a brown color. The composition was hydrophilic and water soluble.

EXAMPLE 27 Hydrophilic Stable Silver-Based Solution

To further demonstrate the light stability of a hydrophilic silver-based composition in solution form, 100 grams of polyethylene glycol (molecular weight: 600) was mixed with 2.7 ml of a 1 meq/ml solution of silver nitrate dissolved in water and 12 ml of a 3 meq/ml solution of sodium chloride. The mixture was stirred overnight producing a clear solution with no precipitate. This solution was stored in a clear non-colored bottle where it was exposed to daily ambient light for a period of greater than two (2) years. Throughout this period, no discoloration of the composition was noted. (Note: The 'two year' period represents from the time when the composition was made to the present. There is no indication that the composition will begin to discolor. Therefore, it is felt that this composition has indefinite photostability.) This composition has a low viscosity and can be used topically on the skin for the prevention and treatment of infections or can be used to make medical devices infection resistant by painting, spraying or dipping. The composition was hydrophilic and water soluble.

EXAMPLE 28 Hydrophilic Stable Silver-Based Solution

As a further demonstration of the light stability of a hydrophilic silver-based composition in solution form, 100 grams of polyethylene glycol (molecular weight: 600) was mixed with 2.7 ml of a 1 meq/ml solution of silver nitrate dissolved in water and 16 ml of a 3 meq/ml solution of sodium chloride. The mixture was stirred overnight producing a clear solution with no precipitate. This solution was also stored in a clear, non-colored bottle where it was exposed to daily ambient light for a period greater than one year, nine months. Throughout this period, no discoloration or the composition was noted. (Note: The 'one year, nine month' time period represents from the time when the composition was made to the present. There is no indication that the composition will begin to discolor. Therefore, it is felt that this composition has indefinite photostability.) This composition has a low viscosity and can be used topically on the skin for the prevention and treatment of infections or can be used to make medical devices infection resistant by painting, spraying or dipping. The composition was hydrophilic and water soluble.

EXAMPLE 29 Hydrophilic Stable Silver-Based Solution

In another demonstration of the light stability of a hydrophilic silver-based composition in solution form, 182 grams of polyethylene glycol (molecular weight: 400) was mixed with 1.8 ml of a 1 meq/ml solution of silver nitrate dissolved in water and 16.2 ml of a 2 meq/ml solution of sodium chloride. The mixture was stirred for one hour producing a clear solution with no precipitate. This solution was also stored in a clear, non-colored bottle where it was exposed to daily ambient light for a period of greater than two years, two months. Throughout this period, no discoloration of the composition was noted. (Note: The 'two years, two months' time period represents from the time when the composition was made to the present. There is no indication that the composition will begin to discolor. Therefore, it is felt that this composition has indefinite photostability.) The above composition underwent antimicrobial testing, demonstrating antimicrobial efficacy against *Staphylococcus aureus, Staphylococcus epidermidis, Escherichia coli,* and *Pseudomonas aeruginosa.* This composition has a low viscosity and can be used topically on the skin for the prevention and treatment of infections or can be used to make medical devices infection resistant by painting, spraying or dipping. The composition was hydrophilic and water soluble.

EXAMPLE 30 Hydrophobic Stable Silver-Based Ointment

To demonstrate a light stable silver-based composition that was in the form of a hydrophobic ointment, a silver-based composition was made by mixing 100 gm of polyethylene glycol (molecular weight: 600) with 0.58 ml of a 5 meq/ml silver nitrate solution in water and 6.25 ml of a 4 meq/ml solution of sodium chloride in water. This mixture was stirred overnight producing a clear solution. 10 gm of this solution was added to 40 gm of melted USP white petrolatum. This composition was mixed until the petrolatum had cooled and solidified to make a silver-based ointment that was resistant to being removed when washed with water. This ointment had the appearance of white petrolatum and was light stable, and antimicrobial.

EXAMPLE 31 Hydrophobic Unstable Silver-Based Ointment

To demonstrate a hydrophobic silver-based ointment that was not photostable or anti-microbial, 0.058 gm of 5 meq/ml silver nitrate solution in water was added to 50 gm of melted USP white petrolatum. This composition was mixed until the petrolatum had cooled and solidified to make a silver-based ointment that was resistant to being removed when washed with water was photo-unstable, and had insignificant antimicrobial activity.

EXAMPLE 32 Silver-Based Composition using Silver Sulfadiazine as Source of Silver Cations To further demonstrate the principle of the invention that the source of the silver ions can be from both water soluble and essentially water insoluble silver salts, a silver composition was made in which the silver ion came from silver sulfadiazine (F.W.: 357). Silver sulfadiazine is water insoluble (i.e., solubility of much below 1 gm/1 L water). In this example, 18.2 grams of polyethylene glycol (molecular weight: 600) was mixed with 0.16 meqs (57 mg) of silver sulfadiazine, and 1.28 ml of aqueous 2 meq/ml sodium thiocyanate solution was added. The mixture was stirred for 1 hour. The resulting composition was clear with no precipitate, and was light-stable. When this composition was applied to a cotton gauze pad and exposed to light, no discoloration occurred.

EXAMPLE 33 Silver-Based Composition Using Silver Chloride as Source of Silver Cations To further demonstrate the principle of the invention that the source of the silver ions can be from both water soluble and essentially water insoluble silver salts, a silver composition was made in which the silver ion came from silver chloride (F.W.: 143.34). Silver chloride is essentially water-insoluble with a solubility of $8.9 \times 10^{-5}$ gm/100 gm water (*CRC Handbook of Chemistry and Physics,* College Edition, 49th Edition, 1968–69, Editor Robert C. Weast). In this example, 18.2 grams of polyethylene glycol (molecular weight: 600) was mixed with 0.16 meqs (23 mg) of silver chloride, and 1.28 ml of aqueous 2 meq/ml sodium thiocyanate solution was added. The mixture was stirred for 1 hour. The resulting composition was clear with no precipitate, and was light-stable. When this composition was applied to a cotton gauze pad and exposed to light, no discoloration occurred.

EXAMPLE 34 Silver-Based Compositions Using Silver Sulfate as Source of Silver Cations To further demonstrate the principle of the invention that the source of the silver ions can be from both water-soluble and essentially water-insoluble silver salts, a silver composition was made in which the silver ion came from silver sulfate (F.W.: 311.8). Silver sulfate is essentially water-insoluble with a solubility of $5.7 \times 10^{-1}$ gm/100 gm water (*CRC Handbook of Chemistry and Physics,* College Edition, 49th Edition, 1968–69, Editor Robert C. Weast). In this example, 18.2 grams of polyethylene glycol (molecular weight: 600) was mixed with 0.16 meqs (25 mg) of silver sulfate, and 2 ml of aqueous 2 meq/ml sodium chloride was added. The mixture was stirred for 1 hour. The resulting composition was clear with no precipitate, and was light-stable. When this composition was applied to a cotton gauze pad and exposed to light, no discoloration occurred.

EXAMPLE 35 Silver-Based Composition Using Silver Benzoate as a Source of Silver Cations To further demonstrate the principle of the invention that the source of the silver ions can be from both water-soluble and essentially water-insoluble silver salts, a silver composition was made in which the silver ion came from silver benzoate (F.W.: 228.99). Silver benzoate is essentially water-insoluble with a solubility of $2.62 \times 10^{-1}$ gm/100 gm water (*CRC Handbook of Chemistry and Physics,* College Edition, 49th Edition, 1968–69, Editor Robert C. Weast). In this example, 18.2 grams of polyethylene glycol (molecular weight: 600) was mixed with 0.16 meqs (36.6 mg) of silver benzoate, and 2 ml of aqueous 2 meq/ml sodium chloride solution was added. The mixture was stirred for 1 hour. The resulting composition was clear with no precipitate, and was light-stable. When this composition was applied to a cotton gauze and exposed to light, no discoloration occurred.

EXAMPLE 36 Silver-Based Composition Using Silver Iodide as Source of Silver Cations To further demonstrate the principle of the invention that the source of the silver ions can be from both water-soluble and essentially water-insoluble silver salts, a silver composition was made in which the silver ion came from silver iodide (F.W.: 234.77). Silver iodide is essentially water-insoluble with a solubility of $2.8 \times 10^{-7}$ gm/100 gm water (*CRC Handbook of Chemistry and Physics,* College Edition, 49th Edition, 1968–69, Editor Robert C. Weast). In this example, 18.2 grams of polyethylene glycol (molecular weight: 600) was mixed with 0.16 meqs (37.6 mg) of silver iodide, and 2 ml of aqueous 2 meq/ml sodium chloride solution was added. The mixture was stirred for 1 hour. The resulting composition was clear with no precipitate, and was light-stable. When this composition was applied to a cotton gauze pad and exposed to light, no discoloration occurred.

EXAMPLE 37 Silver-Based Composition Using Silver Oxide as Source of Silver Cations To further demonstrate the principle of the invention that the source of the silver ions can be from both water-soluble and essentially water-insoluble silver salts, a silver composition was made in which the silver ion came from silver oxide (F.W.: 231.74). Silver oxide is essentially water-insoluble with a solubility of $1.3 \times 10^{-3}$ gm/100 gm water (*CRC Handbook of Chemistry and Physics*, College Edition, 49th Edition, 1968–69, Editor Robert C. Weast). In this example, 18.2 grams of polyethylene glycol (molecular weight: 600) was mixed with 0.16 meqs (18.5 mg) of silver oxide, and 2 ml of aqueous 2 meq/ml sodium chloride solution was added. The mixture was stirred for 1 hour. The resulting composition was clear with no precipitate, and was light-stable. When this composition was applied to a cotton gauze and exposed to light, no discoloration occurred.

EXAMPLE 38 Silver-Based Composition Using Silver Thiocyanate as Source of Silver Cations To further demonstrate the principle of the invention that the source of the silver ions can be from both water-soluble and essentially water-insoluble silver salts, a silver composition was made in which the silver ion came from silver thiocyanate (F.W.: 165.95). Silver thiocyanate is essentially water-insoluble with a solubility of $2.1 \times 10^{-5}$ gm/100 gm water (*CRC Handbook of Chemistry and Physics*, College Edition, 49th Edition, 1968–69, Editor Robert C. Weast). In this example, 18.2 grams of polyethylene glycol (molecular weight: 600) was mixed with 0.16 meqs (26.5 mg) of silver thiocyanate, and 2 ml of aqueous 2 meq/ml sodium chloride solution was added. The mixture was stirred for 1 hour. The resulting composition was clear with no precipitate, and was light-stable, When this composition was applied to a cotton gauze and exposed to light, no discoloration occurred.

EXAMPLE 39 Silver-Based Composition Using Silver Bromide as Source of Silver Cations To further demonstrate the principle of the invention that the source of the silver ions can be from both water-soluble and essentially water-insoluble silver salts, a silver composition was made in which the silver ion came from silver bromide (F.W.: 187.8). Silver bromide is essentially water-insoluble with a solubility of $8.4 \times 10^{-6}$ gm/100 gm water (*CRC Handbook of Chemistry and Physics*, College Edition, 49th Edition, 1968–69, Editor Robert C. Weast). In this example, 18.2 grams of polyethylene glycol (molecular weight: 600) was mixed with 0.16 meqs (30 mg) of silver bromide, and 2 ml of aqueous 2 meq/ml sodium chloride solution was added. The mixture was stirred for 1 hour. The resulting composition was clear with no precipitate, and was light-stable. When this composition was applied to a cotton gauze and exposed to light, no discoloration occurred.

EXAMPLE 40 Silver-Based Composition Using Silver Carbonate as a Source of Silver Cations To further demonstrate the principle of the invention that the source of the silver ions can be from both water-soluble and essentially water-insoluble silver salts, a silver composition was made in which the silver ion came from silver carbonate (F.W.: 275.75). Silver carbonate is essentially water-insoluble with a solubility of $3.2 \times 10^{-3}$ gm/100 gm water (*CRC Handbook of Chemistry and Physics*, College Edition, 49th Edition, 1968–69, Editor Robert C. Weast). In this example, 18.2 grams of polyethylene glycol (molecular weight: 600) was mixed with 0.16 meqs (22 mg) of silver carbonate, and 2 ml of aqueous 2 meq/ml sodium chloride solution was added. The mixture was stirred for 1 hour. The resulting composition was clear with no precipitate, and was light-stable. When this composition was applied to a cotton gauze and exposed to light, no discoloration occurred.

EXAMPLE 41 Stable Silver-Based Composition Using the Thiocyanate

To demonstrate the principle of the invention, silver compositions were made in which thiocyanate was chosen as the stabilizing anion. In this example, 18.2 grams of polyethylene glycol (molecular weight: 600) was mixed with 0.16 ml of an aqueous 1 meq/ml solution of silver nitrate, dissolved in water, and 0.24 ml of aqueous 2 meq/ml sodium thiocyanate solution was added. The mixture was stirred for 1 hour. The ratio of thiocyanate anions to silver cations was 3.5 to 1. The resulting composition was clear with no precipitate, and was light-stable. When this composition was applied to a cotton gauze pad and exposed to light, no discoloration occurred.

EXAMPLE 42 Unstable Silver-Based Composition Using the Thiocyanate

Again, to demonstrate that excess of anions is of prime importance in stabilizing the antimicrobial compositions of this invention, a silver composition was made in which a thiocyanate anion was used in an equivalent amount to the silver cation. In this example, 18.2 grams of polyethylene glycol (molecular weight:600) was mixed with 0.16 ml of an aqueous 1 meq/ml solution of silver nitrate, dissolved in water, and 0.16 ml of aqueous 1 meq/ml sodium thiocyanate solution was added. The mixture was stirred for 1 hour. The ratio of thiocyanate anions to silver cations was 1 to 1. The resulting composition was cloudy with precipitate. When this composition was exposed to light, the precipitate discolored.

EXAMPLE 43 Stable Silver-Based Foam

To illustrate a method for making a photostable silver-based foam, 20 grams of a polyurethane prepolymer (Hypol 2002, W.R. Grace & Co.) was added, while stirring quickly and thoroughly, into 0.62 ml of a 1 meq/ml of silver nitrate dissolved in water and then was stirred immediately and thoroughly in 9.9 ml of a 1 meq/ml of sodium chloride dissolved in the water (the ratio of chloride anions to silver cations was 16 to 1). The mixture was stirred for approximately 30 seconds. The mixture instantly began to react to form a foam. After 15 minutes, the foam was removed from its container and stored in the dark to allow the foam to dry. A sample of the silver-based foam was photostable when exposed to a plant growth light for more than 24 hours. This silver-based foam can be used for a large variety of medical applications, including an antimicrobial absorptive foam dressing.

EXAMPLE 44 Silver-Based Foam

To further illustrate a method for making a photostable silver-based foam, 20 grams of a polyurethane prepolymer (Hypol 2002, W.R. Grace & Co.) was added, while stirring quickly and thoroughly, into 0.62 ml of a 1 meq/ml of silver nitre dissolved in water and then was stirred immediately and thoroughly in 12.4 ml of a 1 meq/ml of sodium chloride dissolved in the water (the ratio of chloride anions to silver cations was 20 to 1). The mixture was stirred for approximately 30 seconds. The mixture instantly began to react to form a foam. After 15 minutes, the foam was removed from its container and stored in the dark to allow the foam to dry. A sample of the silver-based foam was photostable when exposed to a plant growth light for more than 24 hours. This silver-based foam can be used for a large variety of medical applications, including an antimicrobial absorptive foam dressing.

EXAMPLE 45 Stable Silver-Based Foam

To even further illustrate a method for making a photostable silver-based foam, 20 grams of a polyurethane prepolymer (Hypol 2002, W.R. Grace & Co.) was added, while stirring quickly and thoroughly, into 0.62 ml of a 1 meq/ml of silver nitre dissolved in water and then immediately was stirred thoroughly in 15.5 ml of a 1 meq/ml of sodium chloride dissolved in the water (the ratio of chloride anions to silver cations was 25 to 1). The mixture was stirred for approximately 30 seconds. The mixture instantly began to react to form a foam. After 15 minutes, the foam was removed from its container and stored in the dark to allow the foam to dry. A sample of the silver-based foam was photostable when exposed to a plant growth light for more than 24 hours. This silver-based foam can be used for a large variety of medical applications, including an antimicrobial absorptive foam dressing.

EXAMPLE 46 Stable Silver-Based

To further illustrate a method for making a photostable silver-based foam, 20 grams of a polyurethane prepolymer (Hypol 2002, W.R. Grace & Co.) was added, while stirring quickly and thoroughly, into 0.62 ml of a 1 meq/ml of silver nitre. dissolved in water and then immediately was stirred thoroughly in 20.1 ml of a 1.06 meq/ml of sodium chloride dissolved in the water (the ratio of chloride anions to silver cations was 35 to 1). The mixture was stirred for approximately 30 seconds. The mixture instantly began to react to form a foam. After 15 minutes, the foam was removed from its container and stored in the dark to allow the foam to dry. A sample of the silver-based foam was photostable when exposed to a plant growth light for more than 24 hours. This silver-based foam can be used for a large variety of medical applications, including an antimicrobial absorptive foam dressing.

It will be appreciated that the present invention, as described above, is not limited to the specific compositions shown nor is it limited to the uses of the compositions described. Modifications in the final compositions, for example, in the type of polyether used, the molecular weight, what cations and anions are used, and what process is used for making the composition, are all well within the scope of the appended claims. As will be apparent to those skilled in the art, in the light of the foregoing disclosure, many substitutions, alterations, and modifications, as well as different uses of the compositions, are possible in the practice of this invention without departing from the spirit or scope thereof.

What is claimed is:

1. An antimicrobial composition consisting essentially of
   (a) a stabilizing acyclic polyether polymer;
   (b) silver ion; and
   (c) a stabilizing anion, selected from the group consisting of chloride, bromide, iodide and thiocyanate, wherein the ratio of equivalents of said anion to equivalents of said silver ion is greater than 4 to 1, when said anion is chloride; is greater than 2.1 to 1, when said anion is bromide; and is greater than 1.1 to 1, when said anion is iodide; is greater than 3.5 to 1 when said anion is thiocyanate; and wherein said acyclic polyether polymer is selected from the group consisting of polyethylene glycol block copolymers and polyethyleneglycol mono (nonylphenyl) ether; and wherein said antimicrobial composition has long-term photostability of greater than 72 hours in direct sunlight.

2. An antimicrobial composition consisting essentially of
   (a) a stabilizing acyclic polyether polymer;
   (b) silver ion; and
   (c) thiocyanate, wherein the ratio of equivalents of said thiocyanate to equivalents of said silver ion is greater than 3.5 to 1; and wherein said antimicrobial composition has long-term photostability of greater than 72 hours in direct sunlight.

3. The composition of claim 2, wherein said acyclic polyether polymer is selected from the group consisting of polyethylene glycol, polypropylene glycol, polyethylene glycol block copolymer, polyethyleneglycol mono (nonylphenyl) ether, and polytetramethylene glycol.

4. The composition of claim 2, wherein said acyclic polyether polymer is a polyether urethane.

5. The composition of claim 2, wherein said acyclic polyether polymer has a molecular weight in the range of from 200 to 100,000 daltons.

6. The composition of claim 1, wherein said silver cation is present in the composition in an amount ranging from $1 \times 10^{-6}$ to 1 meq of silver ion per gram of acyclic polyether polymer.

7. The composition of claim 6, wherein said amount of silver ion is in the range of from $1 \times 10^{-3}$ to $1 \times 10^{-1}$ meq of silver ion per gram of acyclic polyether polymer.

8. The composition of claim 1, wherein said acyclic polyether polymer is a polyethylene glycol block copolymer.

9. The composition of claim 8, wherein said polyethylene glycol block copolymer is a poloxamer.

10. The composition of claim 1, wherein said acyclic polyether polymer is polyethyleneglycol mono (nonylphenyl) ether.

11. The composition of claim 1, wherein the ratio of chloride to silver ion is from 9:1 to 100:1.

12. A method of treating infection in a mammal, comprising the step of applying to an infected site of said mammal a disinfecting amount of the antimicrobial composition of claim 1.

13. A method of imparting antimicrobial protection to an object, comprising the step of applying to said object an effective protecting amount of an antimicrobial composition of claim 1.

14. The method of claim 13, wherein said object is a medical device selected from the group consisting of a medical implant, a wound care device, a personal protection device, a body cavity device and a birth control device.

15. The composition of claim 1, wherein the ratio of equivalents of said anion to equivalents of said silver ion is greater than 10 to 1, when said anion is chloride; is greater than 3 to 1, when said anion is bromide; is greater than 1.2 to 1, when said anion is iodide; and is greater than 4 to 1 when said anion is thiocyanate; and wherein said antimicrobial composition has long-term photostability of greater than 72 hours in direct sunlight.

16. The composition of claim 1, wherein the ratio of equivalents of said anion to equivalents of said silver ion is greater than 15 to 1, when said anion is chloride; is greater than 3.5 to 1, when said anion is bromide; is greater than 1.4 to 1, when said anion is iodide; is greater than 5 to 1 when said anion is thiocyanate; and wherein said antimicrobial composition has long-term photostability of greater than 72 hours in direct sunlight.

* * * * *